United States Patent [19]
Komives et al.

[11] Patent Number: 5,510,247
[45] Date of Patent: Apr. 23, 1996

[54] CENTRIFUGAL MULTIPHASE SYSTEMS AND METHOD FOR USING THE SAME

[75] Inventors: Claire Komives, Pittsburgh; Alan J. Russell, Wexford, both of Pa.

[73] Assignee: University of Pittsburgh, Pittsburgh, Pa.

[21] Appl. No.: 38,925

[22] Filed: Mar. 29, 1993

[51] Int. Cl.$^6$ ............................ C12P 1/00; C12S 13/00; C12M 1/40
[52] U.S. Cl. .................. 435/41; 435/262; 435/813; 435/289.1; 435/304.1; 435/283.1
[58] Field of Search .................... 435/2, 4, 19, 21, 435/41, 174, 262, 262.5, 287, 288, 291, 310, 311, 312, 803, 813; 422/72, 101; 494/22, 35, 37; 210/632, 634, 643, 657, 198.2

[56] References Cited

U.S. PATENT DOCUMENTS

| | | | |
|---|---|---|---|
| 2,924,555 | 2/1960 | Reese | 435/813 |
| 3,187,998 | 6/1965 | Madany | 494/22 |
| 4,326,666 | 4/1982 | Fujiwara et al. | 494/22 |
| 4,939,087 | 7/1990 | Van Wie et al. | 435/240.25 |

OTHER PUBLICATIONS

Andersson et al. "Bioconversions in aqueous two-phase systems" Enzyme Microb. Technol. vol. 12 (1990) pp. 242–254.

Ayala et al. "Protein Extraction and Activity in Reverse Micelles of a Nonionic Detergent" Biotech. and Bioeng. vol. 39 (1992) pp. 806–814.

Caldwell et al. "Detoxification of Organophosphate Pesticides . . . " Biotech and Bioeng. vol. 37 (1991) pp. 103–109.

Jorba et al. "Optimization and Kinetic studies of the enzymatic synthesis of Ac–Phe–Leu–NHz in reversed micelles." Enzyme Microb. Technol. vol. 14 (1992) pp. 117–124.

Larsson et al. "Integration of Bioconversion and Downstream Processing . . . " Biotech. and Bioeng. vol. 33 (1989) pp. 758–766.

Lee et al. "Sulfur Removal from Coal Through Membrane Media Containing Biocatalysts." J. Chem. Tech. Biotechnol. vol. 48 (1990) pp. 71–79.

Pfammatter et al. "Solubilization and Growth of *Candida pseudotropicalis* in Water–in–oil Microemulsions". Biotech. and Bioeng. vol. 40 (1992) pp. 167–172.

*Primary Examiner*—William H. Beisner
*Attorney, Agent, or Firm*—Reed Smith Shaw & McClay

[57] ABSTRACT

Centrifugal systems and methods of use thereof are provided. The systems and methods provide two-phase extraction/reaction and separation in a single operational unit. The systems are easily scalable and operable in a continuous manner. Also provided is a system and method for effecting catalytic reactions in an organic/reverse micelle system.

51 Claims, 17 Drawing Sheets

Legend:
- single phase
- unstable macroemulsion
- excess water
- three phases
- excess hexane
- other Legend:  single phase        three phases
         unstable macroemulsion   excess hexane
         excess water          other Legend:
- single phase
- unstable macroemulsion
- excess water
- three phases
- excess hexane
- other Legend:
- single phase
- unstable macroemulsion
- excess water
- three phases
- excess hexane
- other Legend:
- ▦ single phase
- ▦ unstable macroemulsion
- ▦ excess water
- ▩ three phases
- 〰 excess hexane
- ☐ other Legend: single phase • unstable macroemulsion • excess water • three phases • excess hexane • other Legend:
- single phase
- unstable macroemulsion
- excess water
- three phases
- excess hexane
- other

CENTRIFUGAL MULTIPHASE SYSTEMS AND METHOD FOR USING THE SAME

FIELD OF THE INVENTION

The present invention relates to continuous centrifugal systems and method of use of such systems in which an extraction or reaction as well as separation is effected in a single operational unit, and especially to continuous centrifugal extractors/reactors utilizing microemulsions or aqueous/aqueous two phase systems.

BACKGROUND OF THE INVENTION

Multiphase systems are rapidly becoming popular in extraction processes as well as in novel reaction processes.

Such systems are particularly attractive, for example, in extraction of protein. While a number of efficient methods for protein purification with high specificity are available for downstream processing, few methods can be employed for large volume, upstream applications. As a result, much of the protein is lost in early stages of processing. Techniques such as ultrafiltration and various methods of precipitation have been used, but offer only minimal selectivity based on size range, isoelectric point or other properties which are common to a large number of proteins in a mixture. Two-phase extraction systems, on the other hand, offer both high volume production as well as specificity.

Aqueous two-phase systems have been described for the large-scale isolation and purification of proteins and biological analysis. Generally, phase separation is a phenomenon that occurs when two solutions of water-soluble polymers are mixed. Instead of using two polymers, a polymer and a salt solution can be used to form an aqueous two-phase solution. The most commonly used polymers are polyethylene glycol (PEG) and dextran. However, many other polymers have been shown to form two-phase systems. Among the polymer-salt systems, PEG/potassium phosphate and PEG/magnesium sulfate are most frequently used. E. Andersson and B. Hahn-Hagerdal, "Bioconversions in Aqueous Two-phase Systems," Enzyme Mircrob Tchnol., 12: 242–254 (1990).

The technique of two-phase extraction in protein separation involves contacting the two liquid phases with a mixture of proteins. The properties of the phases are such that the desired proteins partition preferably into one of the two layers. These properties may include hydrophobicity, $pK_a$, size, density or any of a number of affinities for the components of a particular phase. Consequent separation of the phases results in containment of the protein(s) of interest in one of the phases. The efficiency of the separation is dependent on the partition coefficients of the proteins, ideally with the protein of interest having the highest partition coefficient of the mixture.

The development of two-phase systems has included the use of affinity ligands to significantly enhance selectivity of protein partitioning. Such affinity ligands include any of a number of entities that preferentially bind a component of interest.

Reactive bioconversions in aqueous two-phase systems have also been described. Biocatalysts (microorganisms, enzymes) can be sensitive to pH, temperature, ionic strength and organic solvents. They are also often expensive. In a chemical/biochemical process, it is therefore desirable to protect them and to be able to reuse them. It is also desirable to obtain a product stream which is as pure and as concentrated as possible.

Extractive bioconversion utilizing two liquid phases with the biocatalyst present in only one of the phases, makes it possible to recover the product from the biocatalyst-free phase. Starch hydrolysis, for example, is a major enzyme-catalyzed process in industrial operation today. The feasibility of carrying out enzymatic starch hydrolysis in aqueous two-phase systems, performing the process in one of the phases and continuously extracting the product to the other phase, has been reported. N. Larson et al., "Integration of Bioconversion and Downstream Processing: Starch Hydrolysis in an Aqueous Two-Phase System," Biotechnology and Bioengineering 33:758–786 (1989).

Recently the principles and applications of two-phase systems have been used in conjunction with reversed micellar technology. M. E. Leser and P. L. Luisi, Chimia 44:270–282 (1990); M. Dekker, Anal. Brochem. 178:217–226 (1990); T. A. Hatton, et al. eds., Surfactant-Based Separation Processes, Marcel Dekker, Inc., 55–90 (1989). Reversed micelles may be described as spontaneously formed spherical aggregates of surfactant molecules in organic solvents. These colloidal systems are formed upon addition of a small volume of water to a much larger volume of immiscible organic solvent(s) containing a surfactant agent.

Reversed micelles, or water-in-oil (W/O) microemulsions, can thus be seen as water droplets solubilized in apolar solvents by virtue of a layer of surfactant molecules. The polar heads of the surfactant molecules are directed toward the interior of the micelles, creating a polar core, where water is localized (i.e., a "water pool").

The water pools of reverse micelles are capable of solubilizing many large hydrophilic molecules including proteins. Protein extraction in a reversed micellar system has been reported, for example, by G. A. Ayala et al. in "Protein Extraction and Activity in Reverse Micelles of a Nonionic Detergent," Biotechnology and Bioengineering, 39:806–814 (1992).

Another important feature of reversed micelles is the differential nature of the polar core and the surrounding medium, especially when composed of hydrocarbon. In designing organic solvent/water systems for biocatalytic reactions, one has to consider the toxicity of the organic solvent for the biocatalyst. In this regard, it has been shown in the last few years that enzymes can be hosted in the water pool of reverse micelles without loss of activity. This observation has attracted considerable interest in the biotechnological areas because of the potential of carrying out biocatalysis in essentially organic solvents as well as protein separation.

The incorporation of enzymes in reversed micelles has thus become a popular method of exploiting their catalytic properties in a predominantly organic environment. The water soluble enzymes are retained in the water droplets, where they maintain their catalytic properties as in bulk aqueous phase. The interest in using micelles as hosts for enzymes lies primarily in the advantages of the continuous organic phase. Many industrially important reactions are limited to organic media because of solubility. Solutes in the organic phase of the micelle system partition into the water pools where they are converted to product by the enzyme. The products, in turn, partition back into the organic bulk phase. In this way, high concentrations of substrate and product can be admitted without inhibitory effects to the enzyme.

Reversed micelles to date have found a number of applications, including some commercial uses. Jorba et al., in "Optimization and Kinetic Studies of Enzymatic Synthesis of Ac-PHE-Leu-NH Subgroup Two in Reversed Micelles," Enzyme Microbiology Technology, 14 (117–124) (February 1992), for example, describe the application of reversed micellar systems in peptide synthesis.

L. Qwang and T. F. Yen, in "Sulphur Removal From Coal Through Multiphase Media Containing Biocatalysts," Journal Chem. Tech. Biotechnol., 48:71–79 (1990), disclose that the sulphur content in coals can be reduced through multiphase media containing biocatalysts such as bacterial cells and cell-free enzyme extracts in a batch process. The results showed that the multiphase processes using biocatalysts have an efficient sulphur removability and a shorter reaction time than conventional microbial processes. Tween 80 was used as a surfactant in the study.

N. Phammatter et al., in "Solubilization and Growth of Candida Pseutotropicalis in Water-In-Oil Microemulsions," Biotechnology and Bioengineering, 40:167–172 (1992), described the growth rate of candida pseudotropicalis in water-in-oil microemulsions in a hexadecane solution containing Tween 85 and Span 80 as surfactant with a limited amount of water therein.

While multiphase extractive and reactive techniques are being demonstrated in principle, demand increases for process systems for larger scale use. Therefore, an important step in developing a process which utilizes a multiphase technique, and particularly reversed micellar systems, for a commercial operation is the design of an efficient continuous system. Several attempts have been made to achieve this goal.

P. Luthi and T. A. Hatton, "Recovery of Biocatalysis Products from Reversed Micellar Reaction Media: A Preliminary Evaluation of Membrane Extractors," Bioseparation, 2:5–14 (1991), for example, demonstrated that ultrafiltration membranes of sufficiently low molecular weight cutoff can be used to retained reversed micelles and their hosted enzymes, while permitting the recovery of lipophilic products of enzymatically-catalyzed, synthesis reactions in a stripping solution on the other side of the membrane. Calculations indicated that hollow fiber membranes having the same rejection characteristics and solvent resistance as the flat sheet membranes, may provide an attractive an efficient means for the recovery of these biosynthesis products.

Chiang and Tsai, in "Application of a Recycled Dialysis System in a Reversed Micellar Reactor," J. Chem. Tech. Biotechnol., 54: 27–32 (1992), disclose the use of a dialysis membrane reactor for integrating reaction and product recovery in reversed micellar systems.

These hollow fiber reactors, recycle dialysis reactors and stirred tank reactors, however, do not provide a satisfactory continuous operation for multiphase systems. The cost and design complexity of the first two reactors render their use in an industrial continuous process unattractive. While the stirred tank reactor design may provide simplicity of design, the requirement of additional equipment to effect separation results in undesirable expense. It is thus desirable to develop multiphase systems that requires only a single unit to effect (1) extraction and/or reaction as well as (2) separation.

Continuous centrifugation has been used in the past for effecting continuous liquid-liquid extraction in a single operational unit.

Also, Van Wie et al., in "A Novel Continuous Centrifugal Bioreactor for High-Density Cultivation of Mammalian and Microbial Cells," Biotechnology and Bioengineering, 38:1190–1202 (1991) and U.S. Pat. No. 4,939,087 disclose a continuous centrifugal bioreactor to study the growth and productivity of dense suspension cultures. The reactor was used in both fermentation and mammalian cell cultivation processes. Van Wie et al. disclose that their reactor can maintain high cell concentrations in a well mixed environment without appreciable cell elutriation. Cells are maintained in the reactor at a desired density by balancing the centrifugal forces with the drag across cell surfaces as media flow is directed radially inward. The reactor is of a tapered shape for better cell retention by providing a large variation in superficial velocity, being of high magnitude at the cone entrance and relatively small values closer to the center of rotation. Because of the angle of taper, the reduction in velocity compensates for the reduced centrifugal forces at small radial distances from the center of rotation. In effect, the centrifugal bioreactor of Van Wie et al. acts to immobilize the cells.

Until the present, however, centrifugation has not been used to effect a multiphase catalytic reaction. Nor has centrifugation been used to effect multiphase extraction of proteins. Nor has centrifugation been used in connection with high affinity extraction means.

It is thus an object of the present invention to provide a centrifugal system for single-stage, multiphase reaction/separation processes. It is also an object of the present invention to provide a continuous centrifugal system for single-stage, multiphase extraction/separation utilizing extraction and high-affinity extraction means in one phase.

SUMMARY OF THE INVENTION

Accordingly, centrifugal systems are provided which can accomplish a, multiphase reaction/separation of products or extraction/separation in a single-stage process. In these systems, centrifugal force maintains substantially separate phases in the vicinity of outlet port(s) of the system, as a result of differences in density between the phases. These systems provide the capability of continuous operation.

In general, the centrifugal reactor system comprises a chamber rotatable about an axis; a means for rotating the chamber about the axis; and at least one inlet means in communicative connection with the chamber for introducing a feed to the chamber. The feed contains at least one reactant. The reactor system also comprises at least one outlet means in communicative connection with the chamber for removing liquid from the chamber.

The reactor chamber contains at least two liquid phases. A first phase comprises a catalyst system partitioned therein. Preferably, the catalyst system is substantially completely or completely partitioned in the first phase.

The catalyst system is selected to effect a desired reaction involving the reactant(s) contained within the feed. The reactant partitions into the first phase to contact the catalyst system and react to produce product(s).

In a preferred embodiment, the product of the reaction partitions to the second phase and is removed from the system.

The chamber is rotated at a tangential velocity to create sufficient centrifugal force to maintain a volume of the second phase as a substantially unmixed phase at the location of communicative connection of the outlet means with the chamber, thereby enabling removal of an amount of the second phase from the chamber while minimizing or completely preventing loss of the catalyst system from the reactor system. Preferably an amount of the second phase is continuously removed to operate the centrifugal reactor system in a continuous manner. The catalyst-containing first phase may be contained within the chamber or withdrawn and recirculated to the reactor chamber.

Preferably the first phase comprises a surfactant and the catalyst system is contained in reversed micelles present within the first phase. The first phase is thus preferably a continuous organic phase. Preferably, the catalyst system comprises an enzyme.

The first phase of the reactor system may comprise an organic lighter phase, and the second phase a heavier aqueous phase. Preferably, the first phase comprises a surfactant rich organic heavier phase, and the second phase comprises a lighter organic phase containing substantially no enzyme.

The two phases of the continuous centrifugal reactor system may also comprise an aqueous/aqueous two-phase system.

Preferably, the continuous centrifugal reactor system further comprises a means for extending contact time between the phases.

The system creates what is essentially a liquid-liquid flow reactor. The system can be used in small scale to test the applicability of the reactor configuration and is easily amenable to process scale-up.

In another embodiment, a centrifugal extractor system is provided, comprising: a chamber rotatable about an axis; a means for rotating the chamber about the axis; at least one inlet means in communicative connection with the chamber for introducing a feed to the chamber; and at least one outlet means in communicative connection with the chamber for removing liquid from the chamber.

The chamber contains at least two liquid phases therein. In a preferred embodiment, the first phase comprises an affinity means selected to preferentially partition at least one constituent of the feed to the first phase. Preferably, the affinity means is selected to substantially completely or completely partition the constituent into the first phase.

The first phase of the system preferably comprises an affinity means such as reversed micelles appropriately chosen for uptake of a protein of interest in a mixture. The first phase may also contain affinity ligands capable of preferentially binding a component of interest.

Alternatively, in an aqueous/aqueous two-phase system, one phase may comprise an aqueous mixture favoring the partitioning of such a protein. A second phase, for example, may contain an aqueous phase of lower density than the first phase, which has lower affinity for the protein than the first phase.

The present centrifugal systems have several advantages over multiphase systems (either extraction systems or reaction systems) currently known. A significant improvement is reduced equipment cost. A single stage accomplishes both the reaction/extraction and separation. Preferably, recycle loops serve to multiply the contact time of the phases, previously accomplished using several extraction units. As a single unit can serve both operations in one, it is easily scaled for both small and large continuous or batch processes.

In still another embodiment, a system for effecting a catalyzed reaction is provided. This system comprises: a reaction vessel; at least one inlet means in communicative connection with the reaction vessel for introducing a feed to the reaction vessel. The feed contains at least one reactant. The reaction vessel also comprises at least one outlet means in communicative connection with the reaction vessel for removing liquid from the reaction vessel.

The reaction vessel contains at least two liquid phases therein. A first phase comprises a surfactant rich organic heavier phase containing reversed micelles. The second phase comprises a light organic phase. The reversed micelles have a catalyst system partitioned therein, which is selected to effect a desired reaction involving the reactant within the feed. The reactant partitions into the first phase to contact the catalyst system and react to produce product. It has been discovered that this organic/reverse micelle system has several advantages over aqueous/reverse micelle systems, including substantially complete or complete partitioning of the reverse micelles into the first phase.

PRESENTLY PREFERRED EMBODIMENTS

A. Continuous Centrifugal Multiphase Bioreaction

The present centrifugal system satisfies the need to develop a simple, yet versatile, system for multiphase techniques. The system is easily scalable and provides the opportunity for continuous processing. A model system is described for the biodegradation of pesticides using phosphotriesterase in reversed micelles of Tween 85.

While there are a number of pollutants found in the soil which are biologically recalcitrant, it has been shown that many organic soil contaminants can be degraded using enzymes. Phosphotriesterase, for example, is an enzyme recently isolated, which degrades organophosphorus pesticides, such and Paraoxon and Parathion, in addition to nerve gases such as Soman and Dimebu. The enzyme hydrolyzes the pesticides at the phosphorus to yield a phosphate diester and p-nitrophenol, as shown in the following chemical equation:

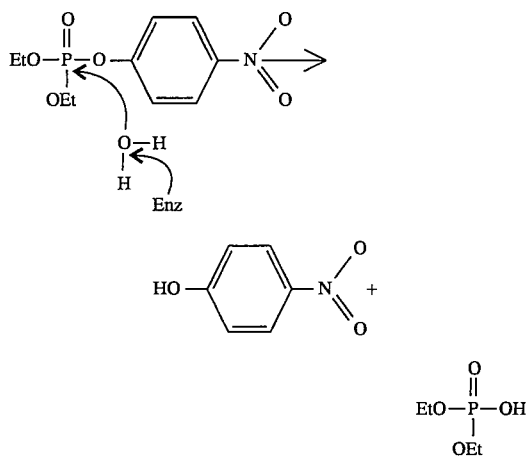

Both of these compounds are more water soluble than the substrate and can be further metabolized by organisms. The enzyme has high catalytic activity, approaching diffusion limitation, with a catalytic rate constant ($k_{cat}$) of 2100 $s^{-1}$. The gene for phosphotriesterase has been isolated and cloned, and it is now possible to produce the enzyme in E. Coli with facility in large quantities.

The activity of this enzyme has been studied in a non-ionic reversed micellar system, composed of polyoxyethylene sorbitan trioleate (Tween 85) with isopropanol or ethylene glycol as cosurfactant in hexane.

Although recent studies have shown the deleterious accumulation of non-ionic surfactants in soil, Tween 85 is completely biodegradable. In fact, it has been used as an additive in fertilizers. While any surfactant system can be chosen for the degradation reactor, the results with Tween 85 suggest the possibility of avoiding addition of harmful chemicals to the environment. Although ionic surfactants such as dioctyl sodium sulfosuccinate (AOT) can be used, previous studies have shown that ionic surfactants in many cases cause rapid degradation of the activity of solubilized proteins.

The presence of Tween 85, in addition to micelle formation at a range of compositions, increases the solubilizing properties of the hexane to dissolve both non-polar and slightly polar organic compounds in high concentrations.

1. Batch Characterization Studies

Figure 1:
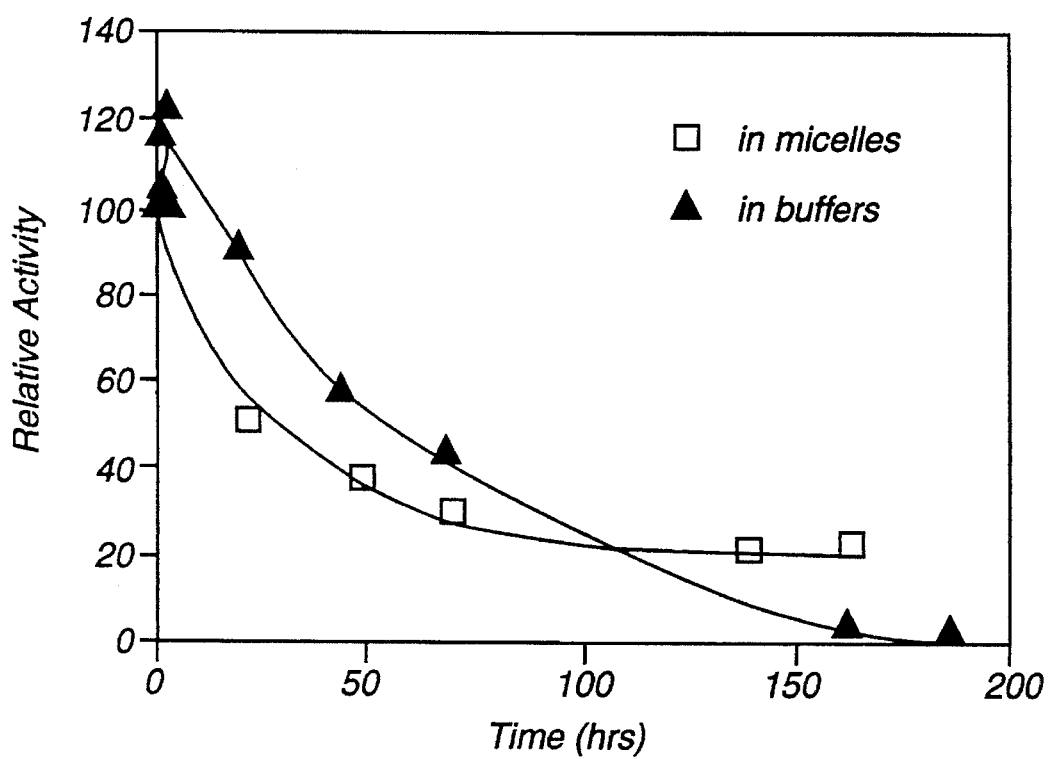
FIG. 1 is an illustration of a comparison of the stability of phosphotriesterase in micelles to its stability in buffer.

Batch studies with the enzyme phosphotriesterase were first performed to characterize the micelle system for the degradation of organophosphorus pesticides. The specific activity of the enzyme was found to approach the value in buffer as the micelle size is increased, while the saturation constant ($K_M$) of the enzyme is increased in the micelles. As shown in Table I below and also in FIG. 1, the stability of phosphotriesterase in the micelles is comparable to that in buffer under some reaction conditions.

TABLE 1

| Solvent | Surfactant | Cosurfactant | Tris-HCl 0.05M | Half Life (Hours) |
|---|---|---|---|---|
| Hexane | Tween 85 0.071M | 1.5 v % isopropanol | 3% v, pH 7 | 60 |
| Hexane | Tween 85 0.071M | 1.5 v % isopropanol | 3% v, pH 8 | 148 |

TABLE 1-continued

| Solvent | Surfactant | Cosurfactant | Tris-HCl 0.05M | Half Life (Hours) |
|---|---|---|---|---|
| Hexane | Tween 85 0.071M | 1.5 v % isopropanol | 3% v, pH 8 | 60 |
| Hexane | Tween 85 0.071M | 1.5 v % isopropanol | 3% v, pH 8 | 125 |
| Hexane | Tween 85 0.071M | 8 v % isopropanol | 1% v, pH 7 | 6 |
| Hexane | Tween 85 0.071M | 8 v % isopropanol | 3% v, pH 7 | 31 |
| Hexane | Tween 85 0.071M | 8 v % isopropanol | 10% v, pH 7 | 40 |
| Cyclohexane | 0.2M Brij 56 | none | 3.6% v, pH 7 | 80 |
| Heptane | 0.1M AOT | " | 3% v, pH 7 | 0.5 |
| Buffer only | | " | pH 7 | 80 |
| Buffer only | | " | pH 8 | 48 |

Characterization studies on the micelle system have included dynamic light scattering (DLS) for determination of apparent micelle size, and the preparation of phase diagrams. Finally, nuclear magnetic resonance spectroscopy (NMR) was used to determine the partition coefficients of the cosurfactant, isopropanol, in the micelle system. The chemical shift of isopropanol is significantly different in water and in hexane. The observed shift in the micelles is dependent on the relative amounts of alcohol in the hexane, water and surfactant volumes.

Spectrophotometric Grade Isopropanol used in the characterization studies was obtained from Mallinckrodt Chemical Co. Hexane and Tween 85 were obtained from Sigma Chemical Co. Paraoxon was synthesized from 4-nitrophenyl phosphorodichloridate and ethanol (punctilious, dehydrated), and purified on a silica gel column with chloroform (Spectrophotometric Grade, Mailinckrodt Chemical Co.). Parathion was purchased from Supelco, Inc. Deuterated Isopropanol-d8 was obtained from Aldrich. Water used in the experiments was distilled and deionized (Milli-Q) and Trizma-base was purchased from Fisher. Phosphotriesterase was purified according procedure of Dumas et al., J. Bio. Chem. 264(33), 19659 (1989), the disclosure of which is incorporated herein by reference. It was stored in a concentrated solution (0.241 ml total protein) at 4° C. and has shown no measurable loss of activity for over 1 year.

Solutions of micelles were prepared in the following manner: 8 ml isopropanol was added to 13 g Tween 85 and Hexane was added to achieve a mixture of 50 ml. Water or Tris-HCl buffer (0.05M, pH 7.0) and hexane were added to this mixture to yield the desired system. For kinetic studies with phosphotriesterase, solutions of equal water content were prepared: one containing enzyme, one containing paraoxon, and one with micelles of Tris-HCl buffer. Appropriate volumes were mixed to fill 1 ml quartz cuvettes, and the reaction was followed in a spectrophotometer. (Perkin Elmer Lambda 3). Michaelis-Menten kinetic constants (discussed below) were found by non-linear regression analysis of the initial rate data.

Enzymes function as catalysts in solution by lowering the free energy of the transition state in a reaction. Like conventional catalysts, the enzyme facilitates the reaction, but is in no way altered, so that when the reaction is completed, it is available to catalyze the conversion of more substrate molecules. When a single substrate is converted to product, the schematic of the reaction can be written

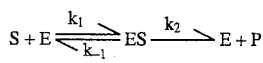

where S and P are substrate and product, respectively, and ES is an enzyme substrate complex. When the substrate concentration is much higher than the enzyme concentration, the enzyme is said to obey the Michaelis-Menten relationship describing the reaction rate, $$V = -\frac{ds}{dt} = \frac{k_2(E)(S)}{(S) + K_M}$$

where (E) is the total enzyme concentration and (S) is the initial substrate concentration. $K_M$ is the saturation constant, and is a function of the individual rate constants, $$K_M = \frac{k_{-1} + k_2}{k_1}$$

$K_M$ has the physical meaning as the substrate concentration which yields half the maximal reaction rate ($V_{max}$), which is dependent on the catalytic rate constant of the chemcial step, $k_2$, as well as the enzyme concentration, $$V_{max} = k_2 \qquad (E)$$

At low substrate concentrations ($S \ll K_M$), the reaction rate follows a linear dependence on S, and reaches the maximum rate, $V_{max}$, at high S when the enzyme is saturated with substrate.

Selected kinetic data for buffer and in micelles at different water contents are presented in Table 2. Initial experiments were performed using paraoxon, parathion and methyl paraoxon. The effect of micelle size, pH, ionic strength and temperature have been investigated.

TABLE 2

| $W_o$ | Vmax μmol/mg/min | $K_M$ (mM) | $k_{cat}(s^{-1})$ | $k_{cat}/K_M$ $mM^{-1}$ $s^{-1}$ |
|---|---|---|---|---|
| | PARAOXON | | | |
| 6.9 | 107 ± 12 | 14.3 ± 3.4 | 70.3 ± 7.9 | 4.9 |
| 30 | 430 ± 28 | 28.9 ± 3.8 | 283 ± 18.4 | 9.8 |
| 45 | 556 ± 80 | 31.2 ± 8.2 | 366 ± 53 | 11.8 |
| 69 | 992 ± 149 | 34.8 ± 9.0 | 653 ± 98 | 18.8 |
| 86 | 1.199 ± 131 | 33.3 ± 6.7 | 789 ± 86 | 23.7 |
| 125 | 1.753 ± 259 | 29.5 ± 8.3 | 1150 ± 170 | 39.1 |
| Tris-HCl | 1.686 ± 42 | 0.019 ± 8% | 1,110 ± 28 | 58,421 |
| | PARATHION | | | |
| 6 | 1.37 ± 0.15 | 81 ± 16 | 0.90 ± 0.10 | 0.011 |
| 29 | 9.7 ± 1.4 | 119 ± 31 | 6.4 ± 0.9 | 0.054 |
| 45 | 14.7 ± 2.4 | 131 ± 36 | 9.7 ± 1.6 | 0.074 |
| 70 | 28 ± 17 | 271 ± 223 | 18 ± 11 | 0.082 |
| 85 | 52 ± 28 | 417 ± 266 | 34 ± 18 | 0.082 |
| Tris-HCl* | 2850 ± 540 | 0.35 ± 0.08 | 1870 ± 360 | 5,340 |
| | METHYL PARAOXON | | | |
| 5.5 | 26.5 ± 2.8 | 17.2 ± 3.2 | 17 | 1.0 |
| 28 | 43.2 ± 2.4 | 15.6 ± 2.0 | 28 | 1.182 |
| 46 | 53.1 ± 3.0 | 15.3 ± 1.9 | 35 | 2.28 |
| 66 | 192 ± 37 | 37.2 ± 11 | 126 | 3.35 |
| 82 | 225 ± 38 | 32.9 ± 8.9 | 148 | 4.5 |
| 122 | 397 ± 111 | 50 ± 19 | 261 | 5.2 |
| TRIS-HCl | 2293 | 0.146 | 1509 | 10,340 |

*10% Methanol added to enhance solubility

Phase diagrams of Tris-HCl buffer (0.05M pH 7)/Hexane/Tween 85 in five different concentrations (all concentrations based on volume %) of isopropanol at room temperature (approximately 20°) are illustrated in FIGS. 2A–2E. The phase diagrams provide guidelines for operating conditions with the micelle system for use in biocatalysis and for extraction purposes. In generating the data for the phase diagrams, twenty mixtures of Tween 85 in hexane with each isopropanol concentration were tested in each of the three temperatures. Tris-HCl buffer was added in 27 increments and after each addition the samples were shaken and allowed to rest to reach equilibrium for 24 hours in the appropriate temperature environment. The samples were observed and the number and type of phases present was recorded. Reversed micelles with Tween 85 are transparent, yet colored, and can be clearly distinguished from hexane and Tris-HCl. Results at 4° C. and 38° C. are set forth in FIGS. 3A–3B and FIGS. 4A–4E.

Such phase diagrams are useful in indicating preferred regions for processing. For batch processes, for example, it is convenient to use a single phase microemulsion. For continuous operation, however, it is preferable to use a two-phase system. Depending on the nature of the reactants and products in a given system, it is necessary that reversed micelles form in equilibrium with aqueous or organic phase. If the products of a reaction are more soluble in an organic phase than in an aqueous phase, one would preferably choose a processing system with an excess organic phase to facilitate product removal.

Figure 5:
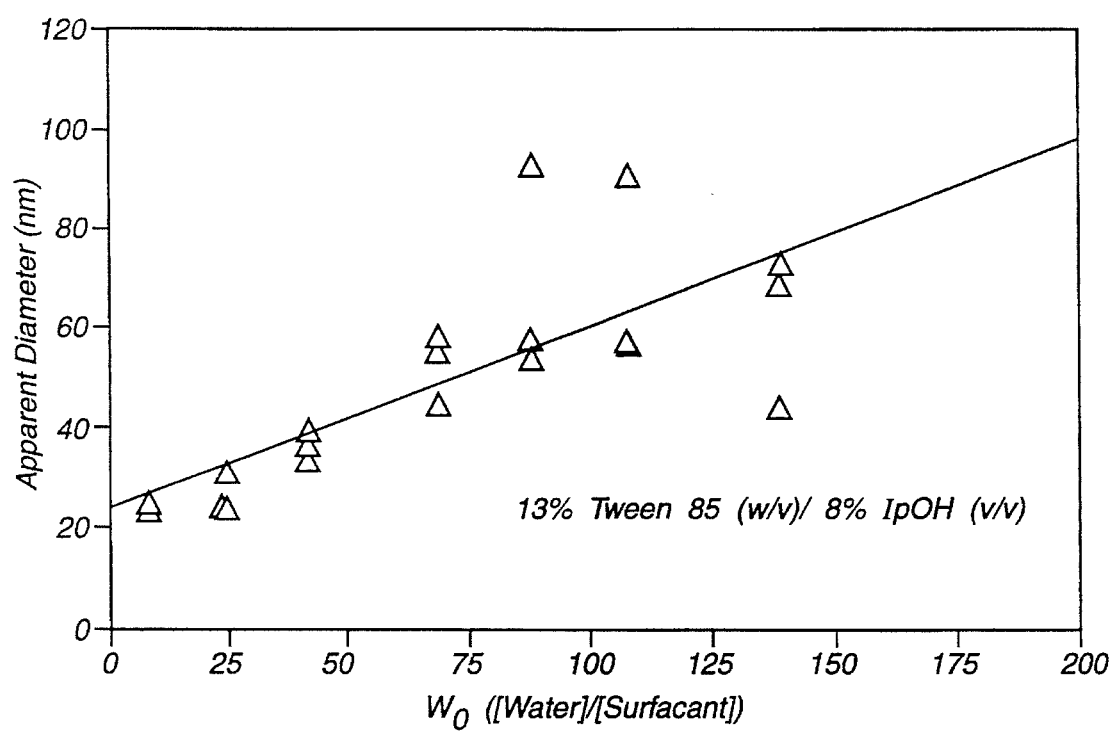
FIG. 5 is an illustration of apparent diameter as a function of water volume.

The apparent translational diffusion coefficient and hydrodynamic radius were measured for micelles containing different volumes of water using dynamic light scattering (DLS). The results of these studies are presented in FIG. 5. The translational diffusion coefficient of the micelles was determined from an auto correlation function of the measured random fluctuations of scattered light intensity. The apparent diameter could be determined using the Stokes - Einstein relation.

Figure 2A:
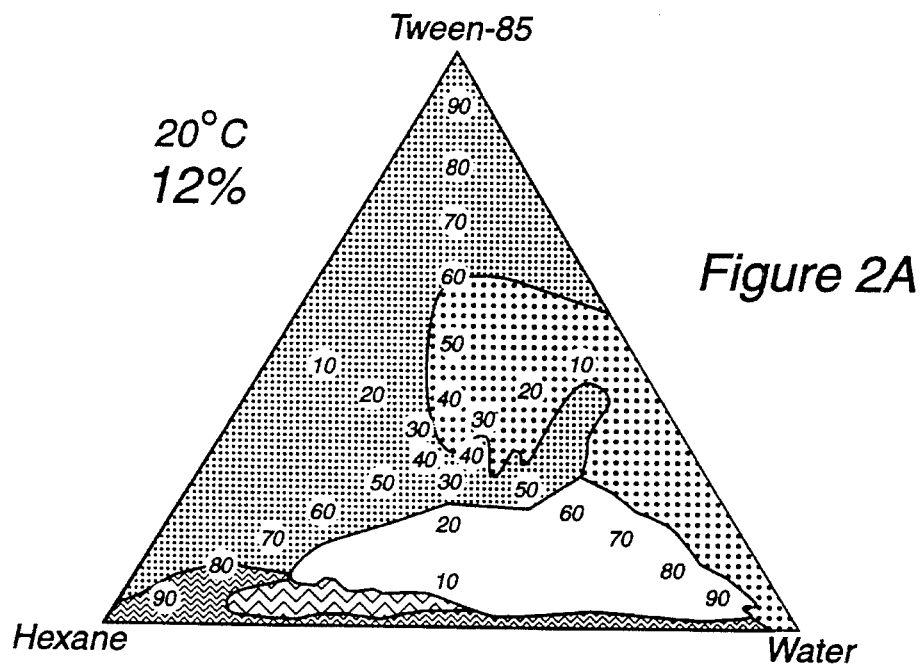
FIGS. 2A–2E are phase diagrams at 20° C. and various isopropanol concentrations.
Figure 2B:
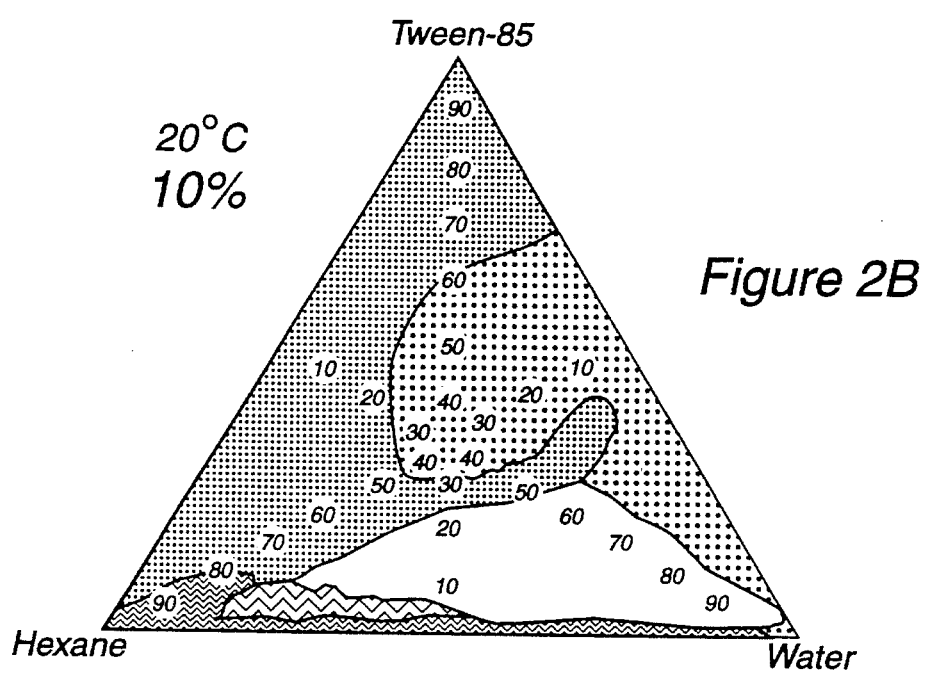
Figure 2C:
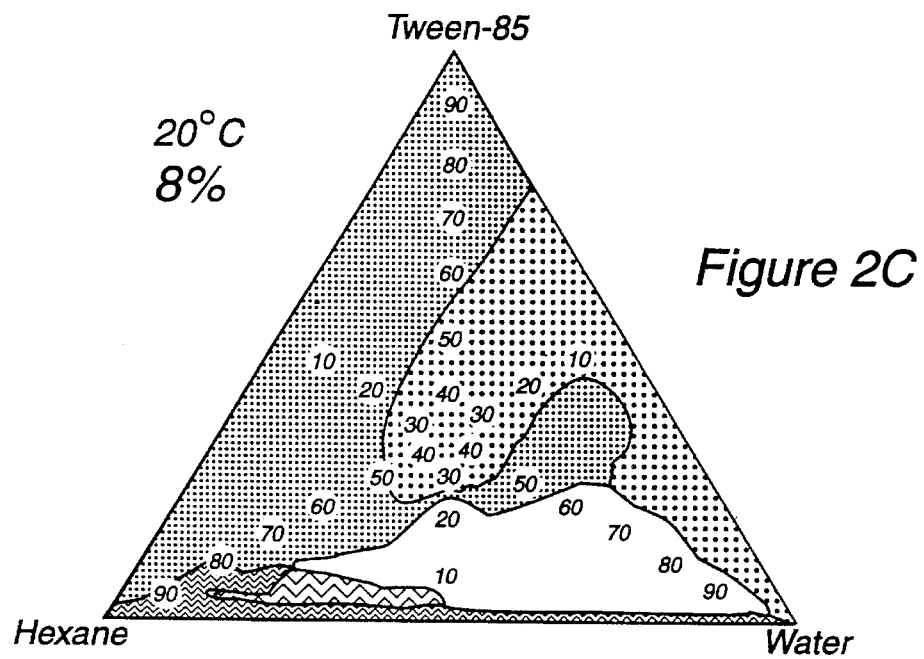
Figure 2D:
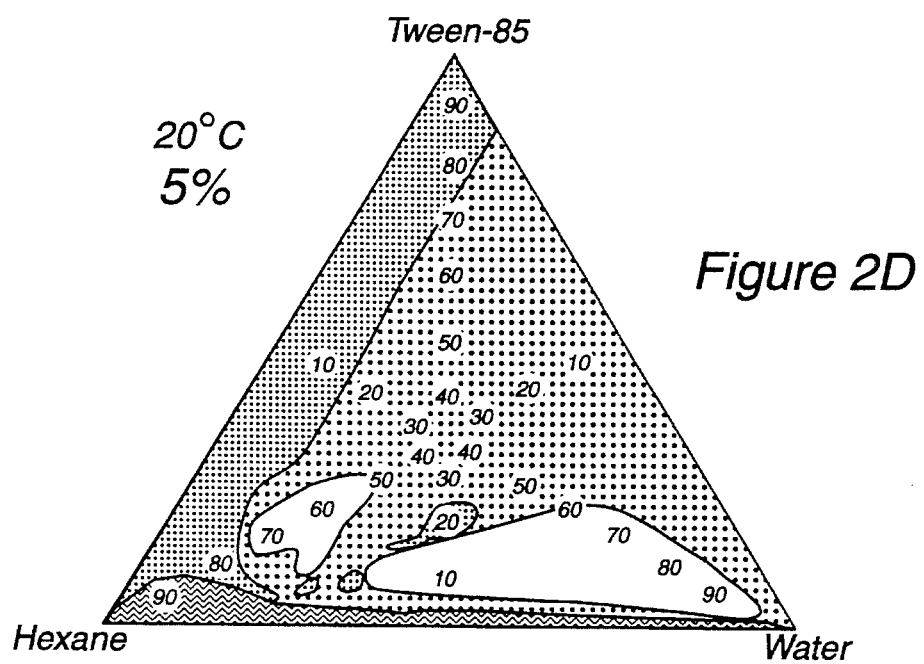
Figure 2E:
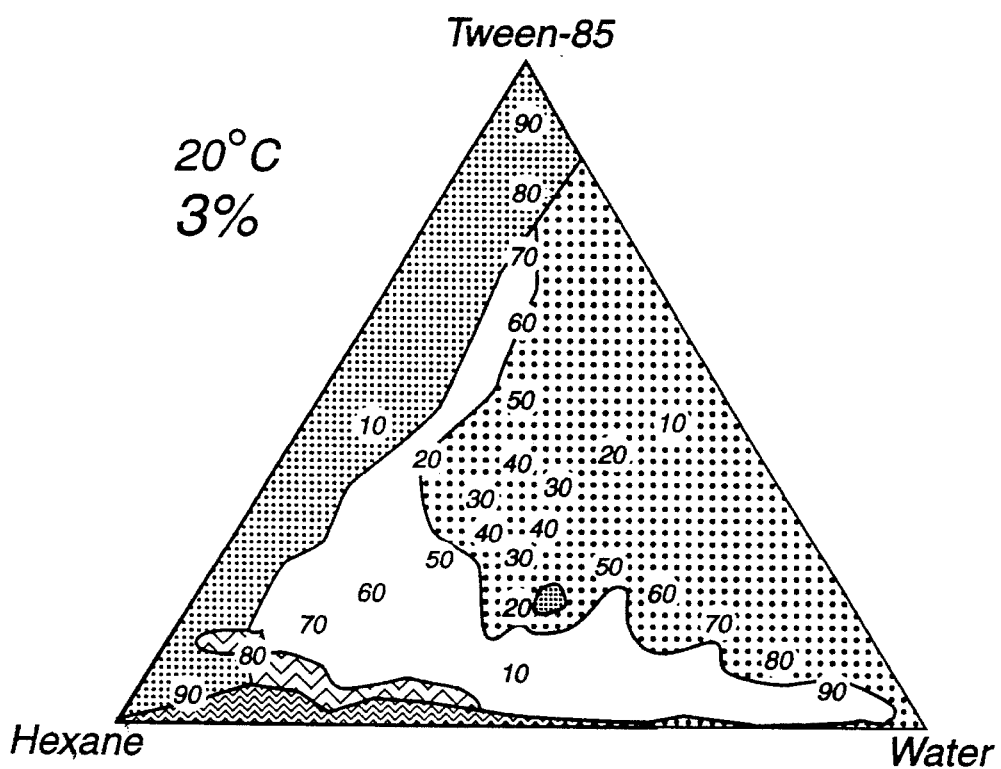
Figure 3A:
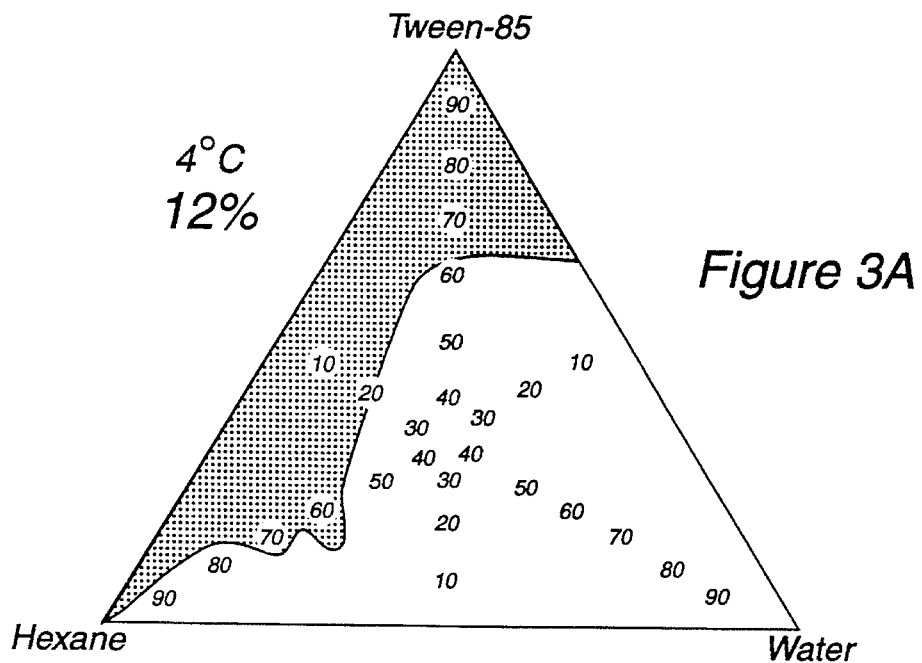
FIGS. 3A–3B are phase diagrams at 4° C. and various isopropanol concentrations.
Figure 3B:
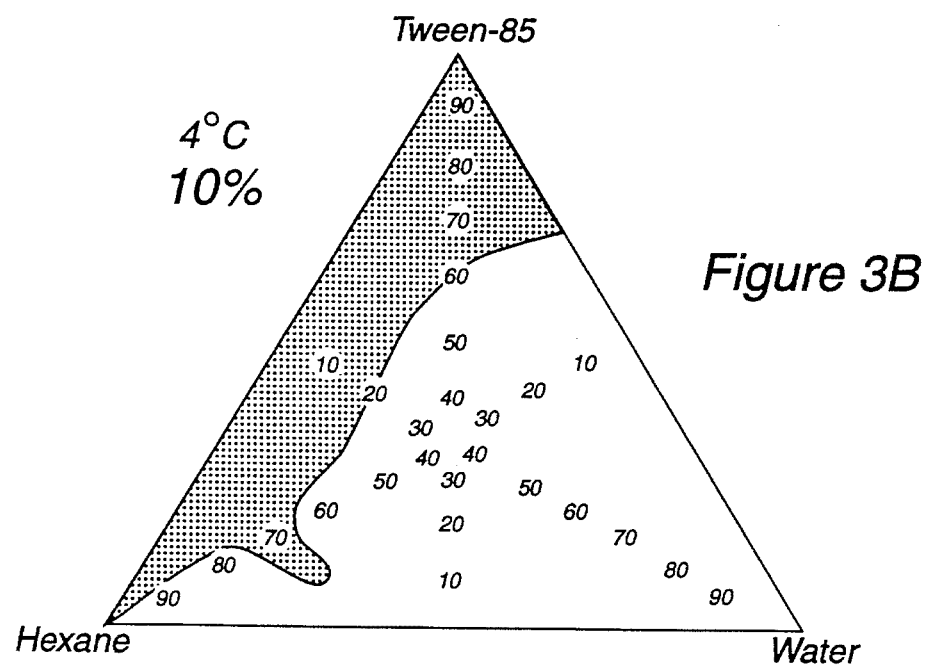
Figure 4A:
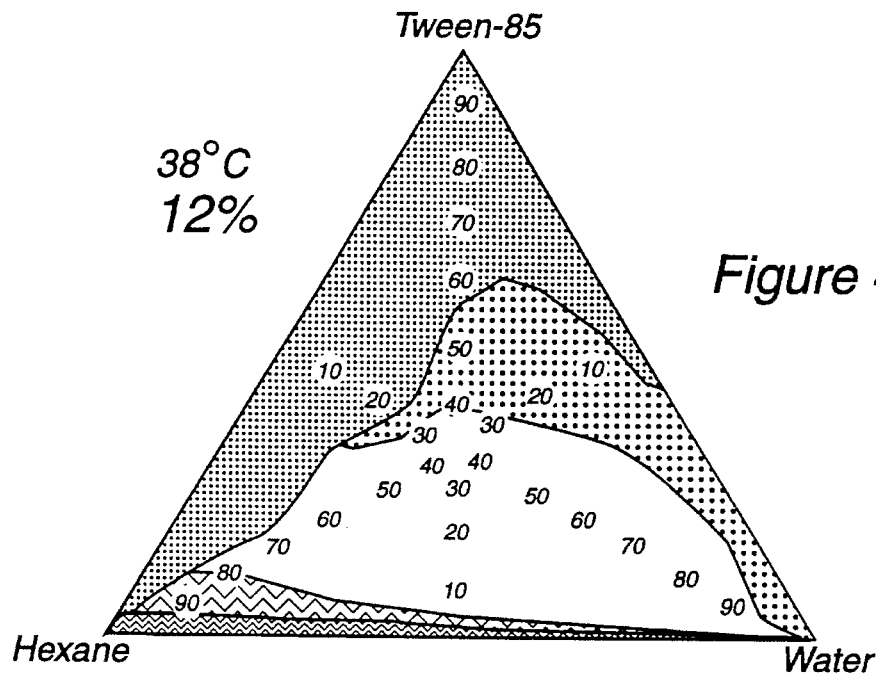
FIGS. 4A–4E are phase diagrams at 38° C. and various isopropanol concentrations.
Figure 4B:
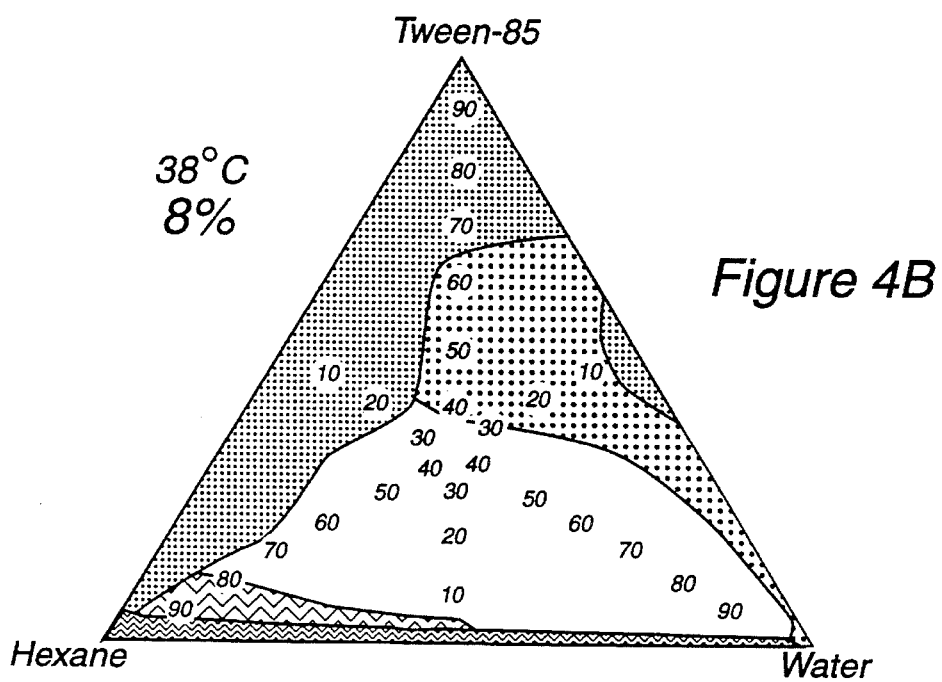
Figure 4C:
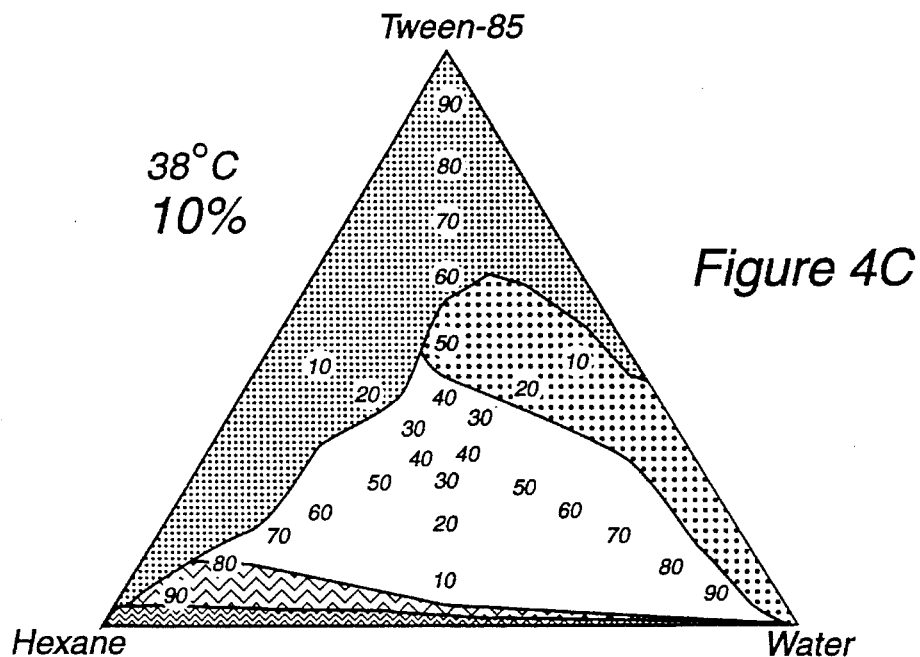
Figure 4D:
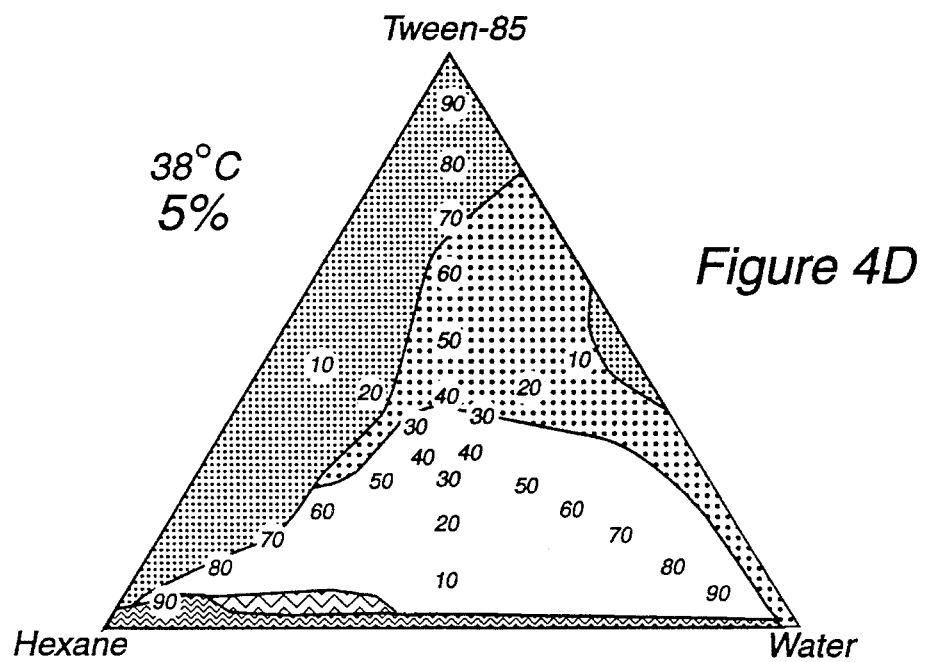
Figure 4E:
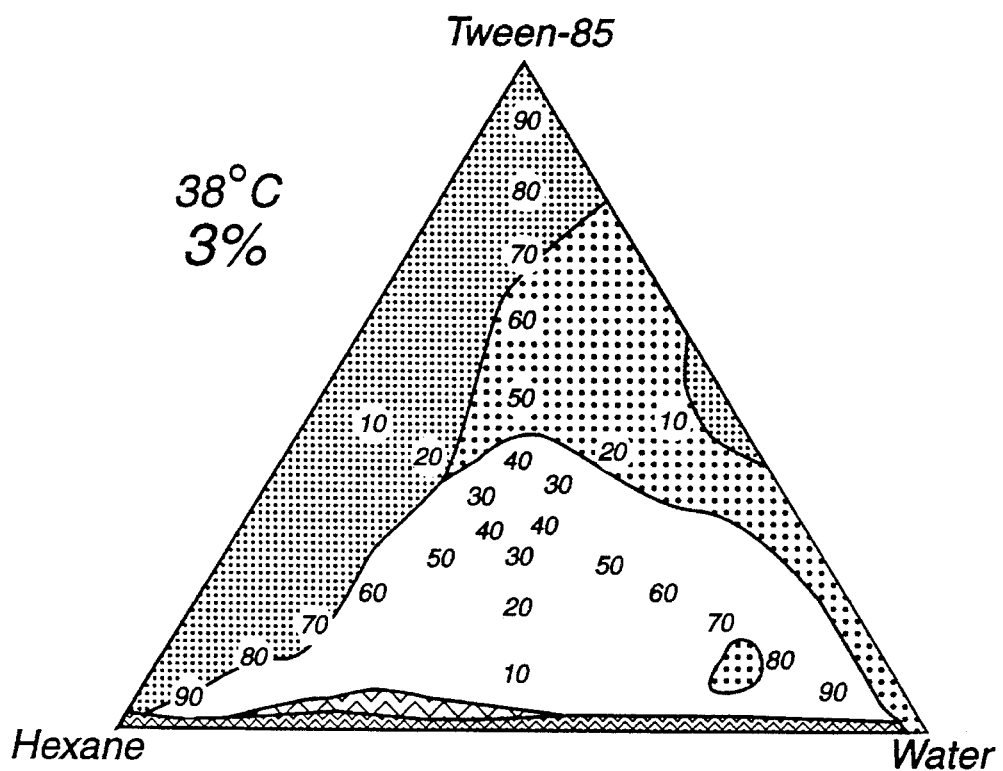
Figure 6:
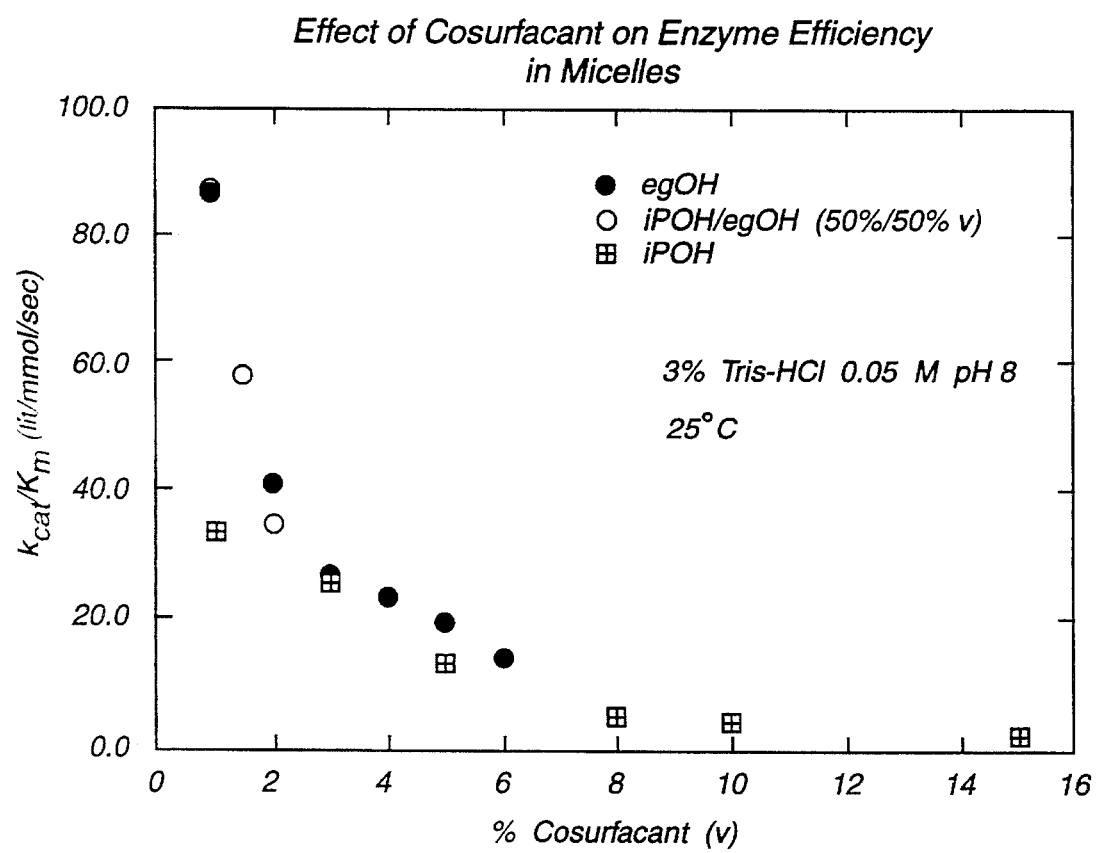
FIG. 6 is an illustration of the effect of cosurfactant on enzyme efficiency in micelles.

From the phase diagrams, it was evident that significant amounts of buffer can be solubilized in micelles of relatively low surfactant and cosurfactant concentrations (See FIG. 2A illustrating the phase diagram of 12% isopropanol at room temperature and FIG. 2C illustrating the phase diagram of 8% isopropanol at room temperature). This result is advantageous as isopropanol was found to reduce the activity of phosphotriesterase in buffer. The optimum conditions appear to be 13% Tween/8% Isopropanol/hexane. In addition studies suggest enhanced enzyme activity in micelles prepared with ethylene glycol as a cosurfactant. The effect of cosurfactant on enzyme efficiency in micelles is illustrated in FIG. 6.

Figure 7:
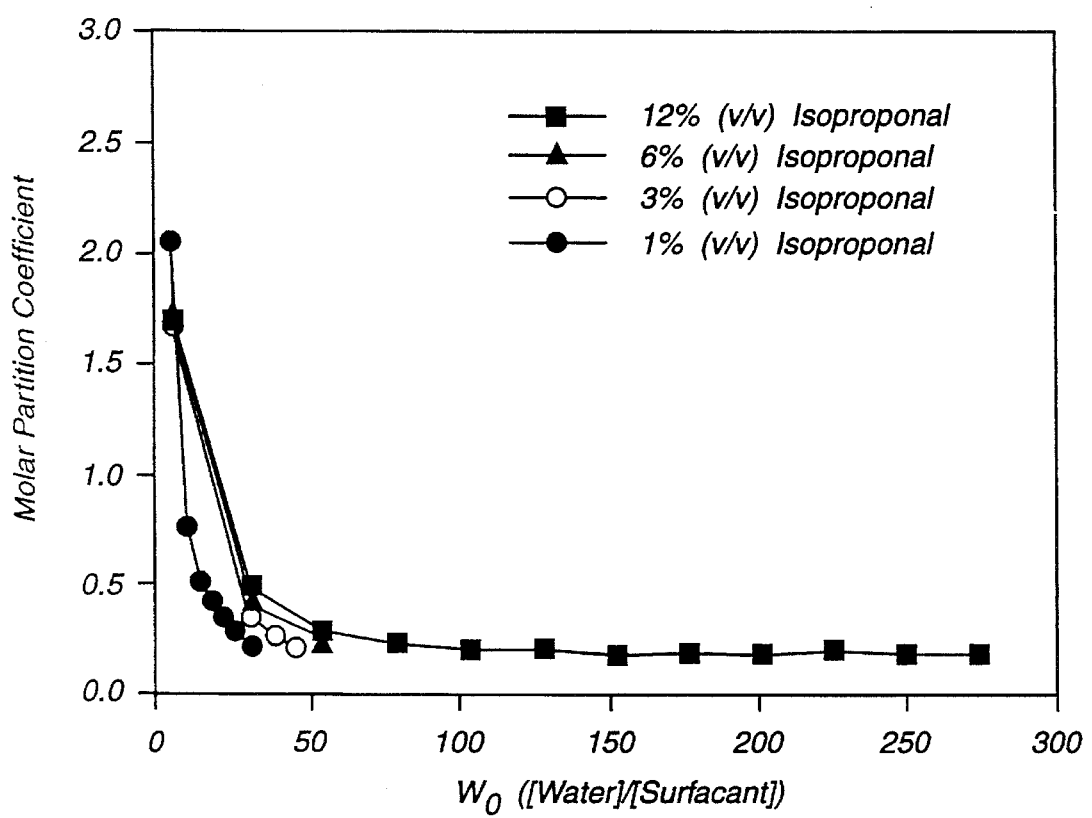
FIG. 7 is an illustration of molar partition coefficient of isopropanol as a function of water content.

Measurement of the partition coefficients of the isopropanol is important because of the effect of the alcohol on the enzyme kinetics. It has been shown that alcohols which are soluble in both the water and organic volumes in micellar systems exchange rapidly between the phases. Nuclear magnetic resonance (NMR) was used to measure the apparent partition coefficients of isopropanol in the hexane and water, neglecting the surfactant layer. The molar partition coefficient of isoproponal as a function of water content is illustrated in FIG. 7.

2. Continuous Centrifugal System Studies

In a continuous multiphase system for catalytic reactions, a feed containing reactant(s) is supplied to the system. The reactant(s) of the feed must be contacted with a catalyst. The catalyst is thus preferably contained within a phase capable of extracting and concentrating the reactant(s).

Generally, a reactive centrifugal system can be operated in two modes:

1. "Flow light phase"—In which a heavy phase contains a catalyst such as an enzyme or biocatalyst and the light phase is organic. The heavy phase can be either contained or continuously drawn and returned to the reactor; or 2. "Flow heavy phase"—In which the heavy phase is aqueous and the light phase contains a catalyst such as an enzyme or biocatalyst. The light phase can be either contained or continuously drawn and returned to the reactor.

Figure 8:
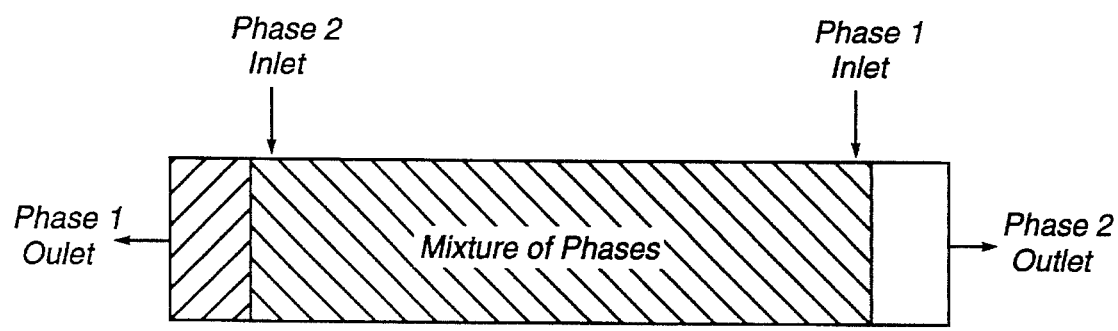
FIG. 8 is an illustration of the desired mixing characteristics of a continuous centrifugal system.

Preferably, mixing of the phases within the reactor is maximized by extending the contact time between the phases, while concurrently effecting separation. To maximize mixing, substantially "pure" (i.e., unmixed) phases should be present in the least volume possible to be removed from the reactor. These substantially unmixed phases preferably exist only in the vicinity of the outlet port(s) of the reactor, while the majority of the volume within the reactor is occupied by a mixture of phases. This result is illustrated schematically in FIG. 8.

In a centrifugal system in which both phases are withdrawn and returned to the reactor a given phase is preferably introduced in the vicinity of the outlet port of the other phase and driven (by virtue of the density difference between the two phases and the applied centrifugal force) in the direction of its own outlet port. The longer the channel length between the respective outlet ports, the greater is the resultant mixing. In general, the reactant containing feed is introduced into the reactor into the phase containing the catalyst system.

In the case where the catalyst containing phase is contained in the reactor rather than continuously withdrawn and returned, the feed is introduced into the phase containing the catalyst and liquid is preferably withdrawn from the other phase at a rate substantially equal to the feed rate. Preferably, reaction products partition to this other phase and are removed from the reactor.

Some reactions may require the flowing of both phases to provide continuous processing. The following enzymatic reaction, for example, requires the flow of both the organic (hexane) light phase and reversed micellar heavy phase

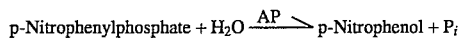

p-Nitrophenylphosphate + H$_2$O $\xrightarrow{\text{AP}}$ p-Nitrophenol + P$_i$

Because the phosphate is insoluble in hexane, it will accumulate in the water pools. The reaction cannot be continuous without removing the lower phase and contacting it with a bulk aqueous phase to partition away the phosphate. In such a case it may be necessary to follow with ultrafiltration of the aqueous phase to retain the enzyme within the system. The product will partition into the hexane phase for continuous removal.

In the case of a continuous multiphase system for biocatalytic degradation and extraction of pesticides from contaminated material (e.g., soil) operating in the mode 2 as described above, an aqueous slurry of pesticide (i.e., reactant) contaminated material is contacted with an organic phase capable of extracting and concentrating the pesticide. The organic phase must be able to support the hydrolysis of the pesticide, and the byproducts of the reaction are preferably resolubilized in the aqueous phase, which should then be removed. The usage of the organic phase is preferably minimized, and organic phase preferably does not leave the reactor. Finally, the process is further complicated by the competing needs for efficient mixing of the phases, and phase separation.

Figure 9:
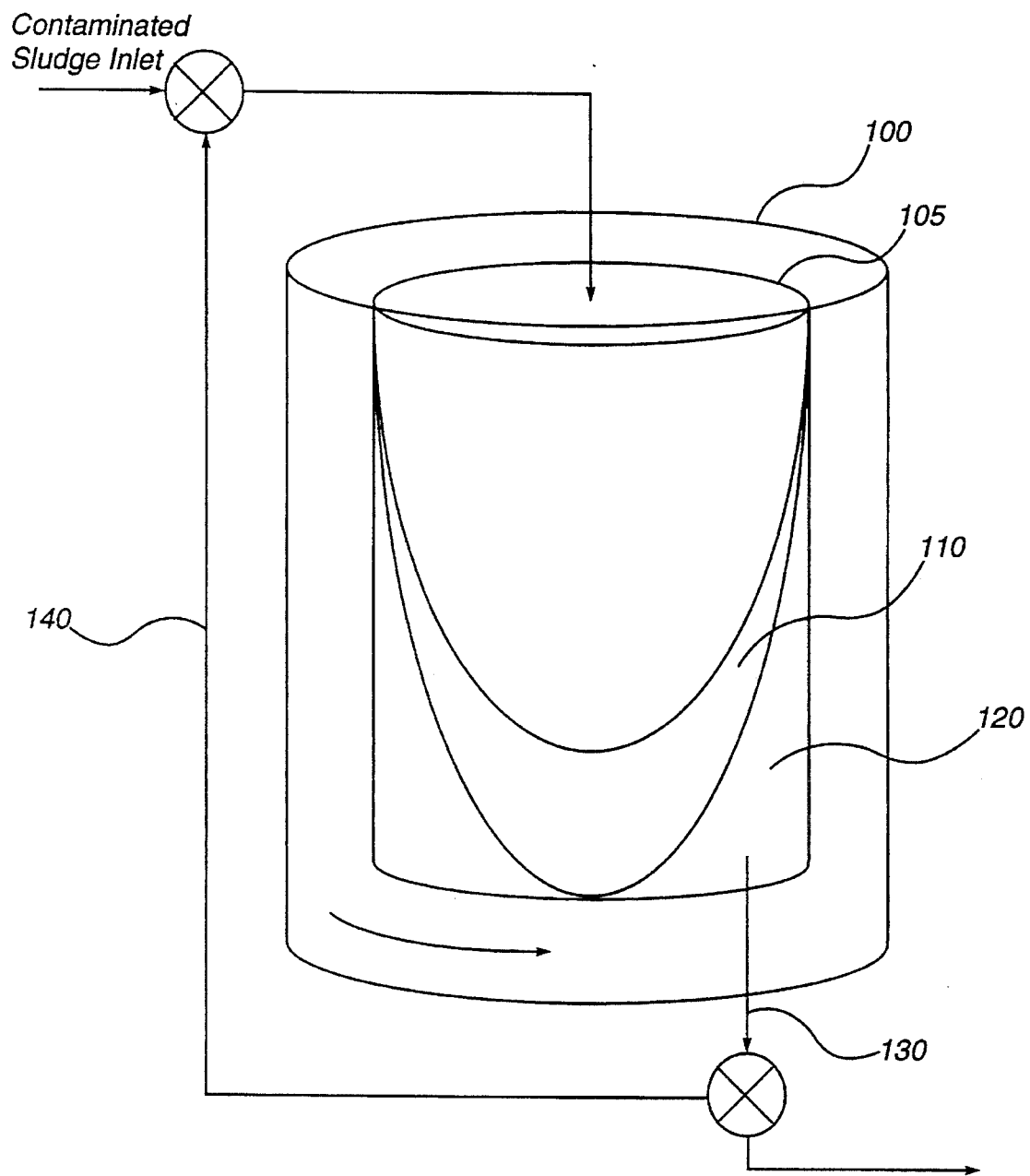
FIG. 9 is a simplified schematic illustration of a continuous centrifugal system.

The operation of such a continuous centrifugal system can be described with reference to FIG. 9, in which a simplified schematic illustration of a continuous centrifugal reactor is presented. In FIG. 9, the fluid within chamber 105 is depicted as a two-phase system throughout, whereas in actual operation a mixture of phases is present within the reactor. As described above, substantially unmixed phases are preferably present only in the vicinity of one or more outlet means.

In operation, reactor feed such as contaminated sludge is fed to reactor 100, which is a centrifuge. Contained within a chamber 105 of reactor 100 is a biphasic micelle mixture, which preferably has reversed micelles of Tween 85 with cosurfactant in hexane in an upper phase 110, and water containing buffer salts, in addition to very low concentrations of Tween 85 (~1x 10$^{-5}$ M)) and cosurfactant in a lower phase 120. Effluent is collected from lower phase 120 via effluent line 130, which will contain the passed sludge. A recycle loop 140 can be employed to enhance the degradation. Recycle loop 140 may be necessary, for example, when using low enzyme concentrations or enzymes with low catalytic rates.

Figure 11:
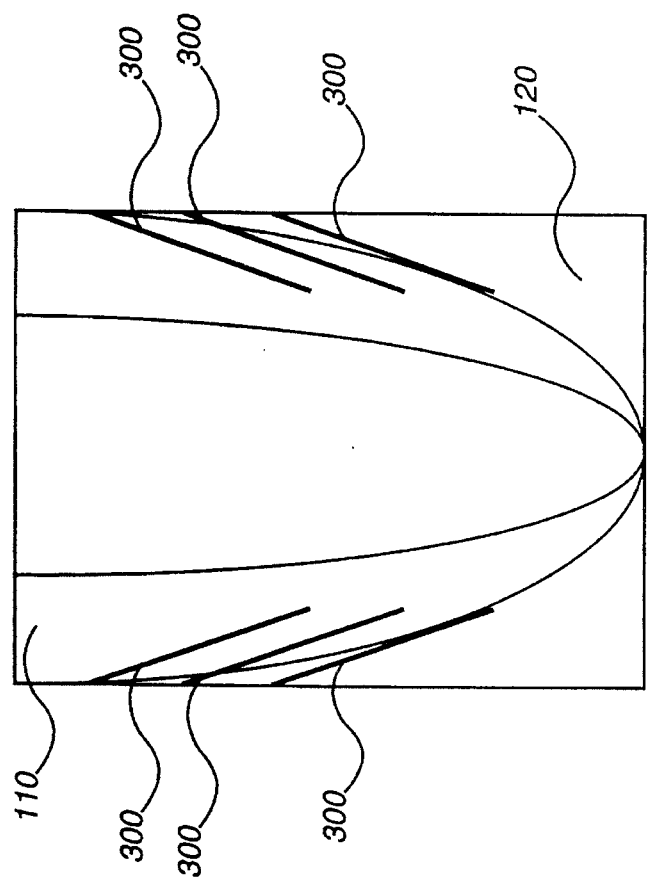
FIG. 11 is a simplified schematic illustration of a continuous centrifugal system incorporating shelves to increase contact time between phases.
Figure 10:
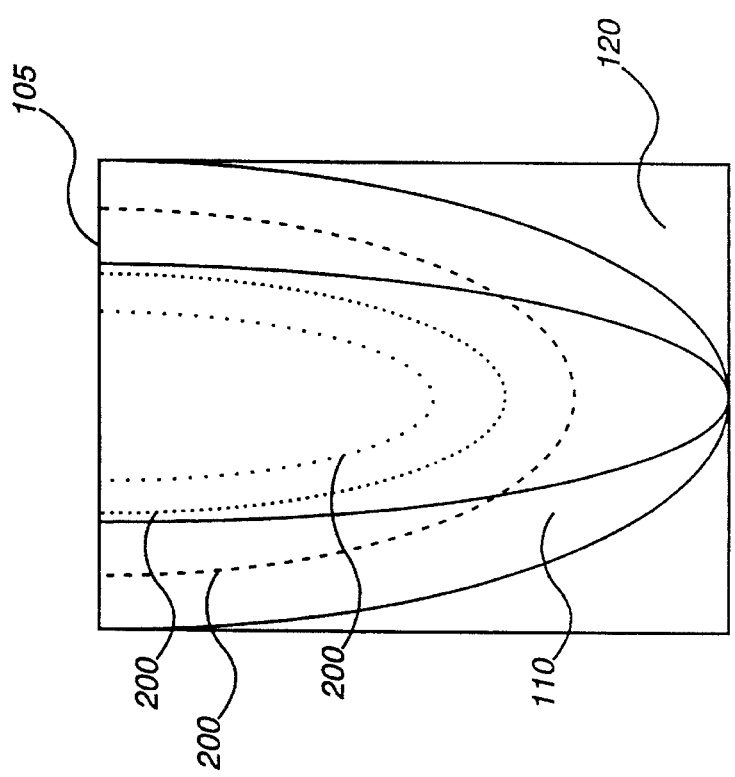
FIG. 10 is a simplified schematic illustration of a continuous centrifugal system incorporating sieves to increase contact time between phases.

Reactor 100 functions to dissolve pesticides and other organics in upper phase 110, by loading the sludge from the top center of chamber 105. It is preferable to increase the contact time of the sludge with upper phase 110. This result can be accomplished using a means for extending contact time such as sieves 200 or shelves or baffles 300 (see FIGS. 10 and 11, respectively) placed in the reactor in such a way as to force the contaminated sludge to pass through upper phase 110 at a slower rate, or several times.

The soil, being the highest density component in reactor 100 will pass to the outer edge of chamber 105. The centrifugal force will aid in separating organic droplets from the soil. These organic droplets will remain in upper phase 110. In this way, the soil that is passed out of reactor 100 is free of organic constituents. The exiting soil will contain only low amounts of Tween 85 and the water soluble cosurfactant in low concentration. In addition, water soluble degradation products will be present in lower phase 120, which will pass out with the sludge via effluent line 130. It, therefore, may be desirable to wash the effluent soil in pure water in an additional step.

The pesticides collected in upper organic layer 110, in addition to other contaminants of interest, are degraded by the enzymes contained there. As organic upper phase 110 will collect compounds passed from the soil, a large scale commercial operation preferably includes a solvent recovery system to distill off the organic solvent (e.g. hexane) for repeated use. In this way, a continuous delivery of fresh hexane and micellar phase components can be delivered to maintain solubilizing capacity. It may also be preferable to collect large rocks and break up heavy, hard chunks from the sludge before feeding, to prevent clogging and destruction of the continuous centrifuge 100.

Figure 12:
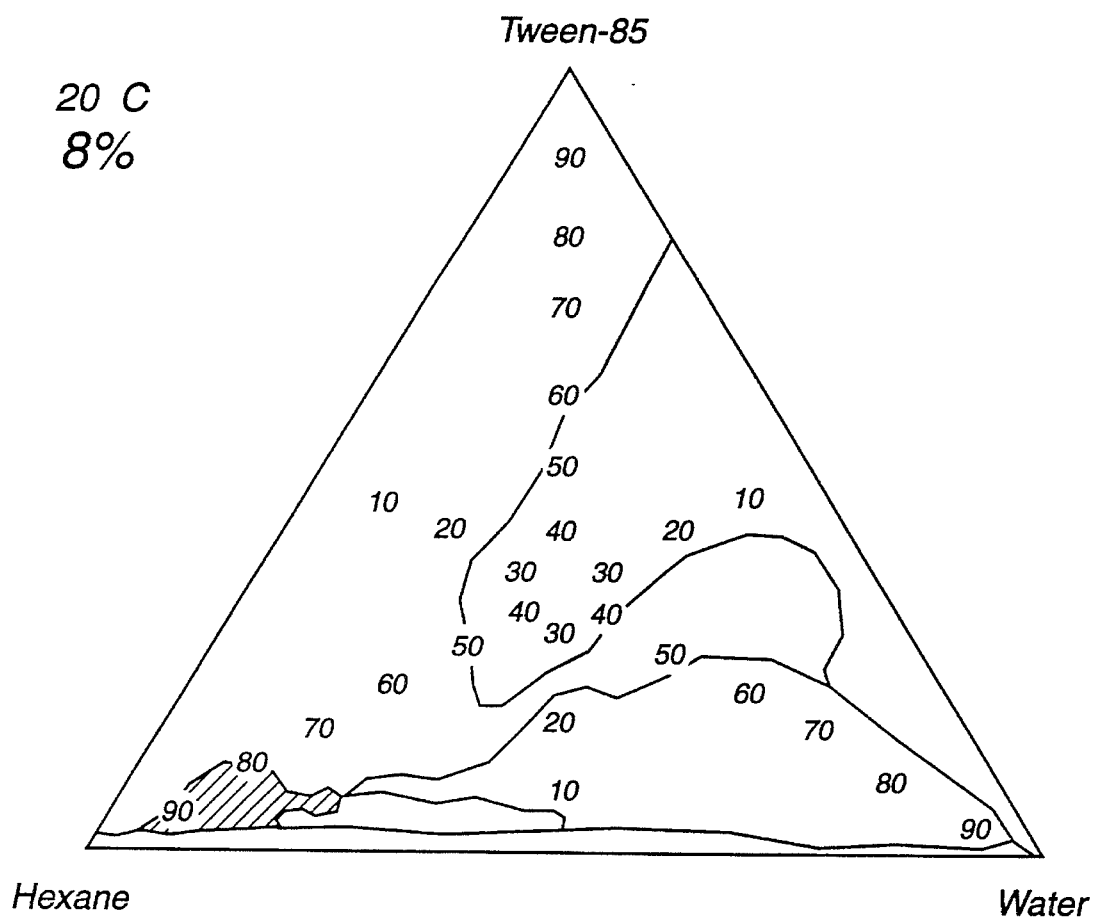
FIG. 12 is an illustration of phase diagram depicting an organic/reverse micelle two-phase region.

As set forth above, if the products of the reaction are more soluble in the organic phase than in an aqueous phase, it is preferable to choose a system with an excess of organic phase to facilitate product removal. Such a region can be found, for example, in FIG. 2C in the lower left hand corner of the phase diagram. This region is illustrated in FIG. 12 as the shaded area.

In this region, close to the single phase region, reverse micelles form with an excess hexane phase which has a low concentration (<15 mM) of Tween with adsorbed water. The enzyme activity for the paraoxon degradation was measured in the Tween rich heavy phase and found to be close to that of buffer, with a K$_{cat}$ of 975 sec$^{-1}$ and a K$_M$ of 32 mM. From activity measurements, it was determined that (within in limits of measurement) no enzyme partitions into the upper hexane phase.

Figure 13:
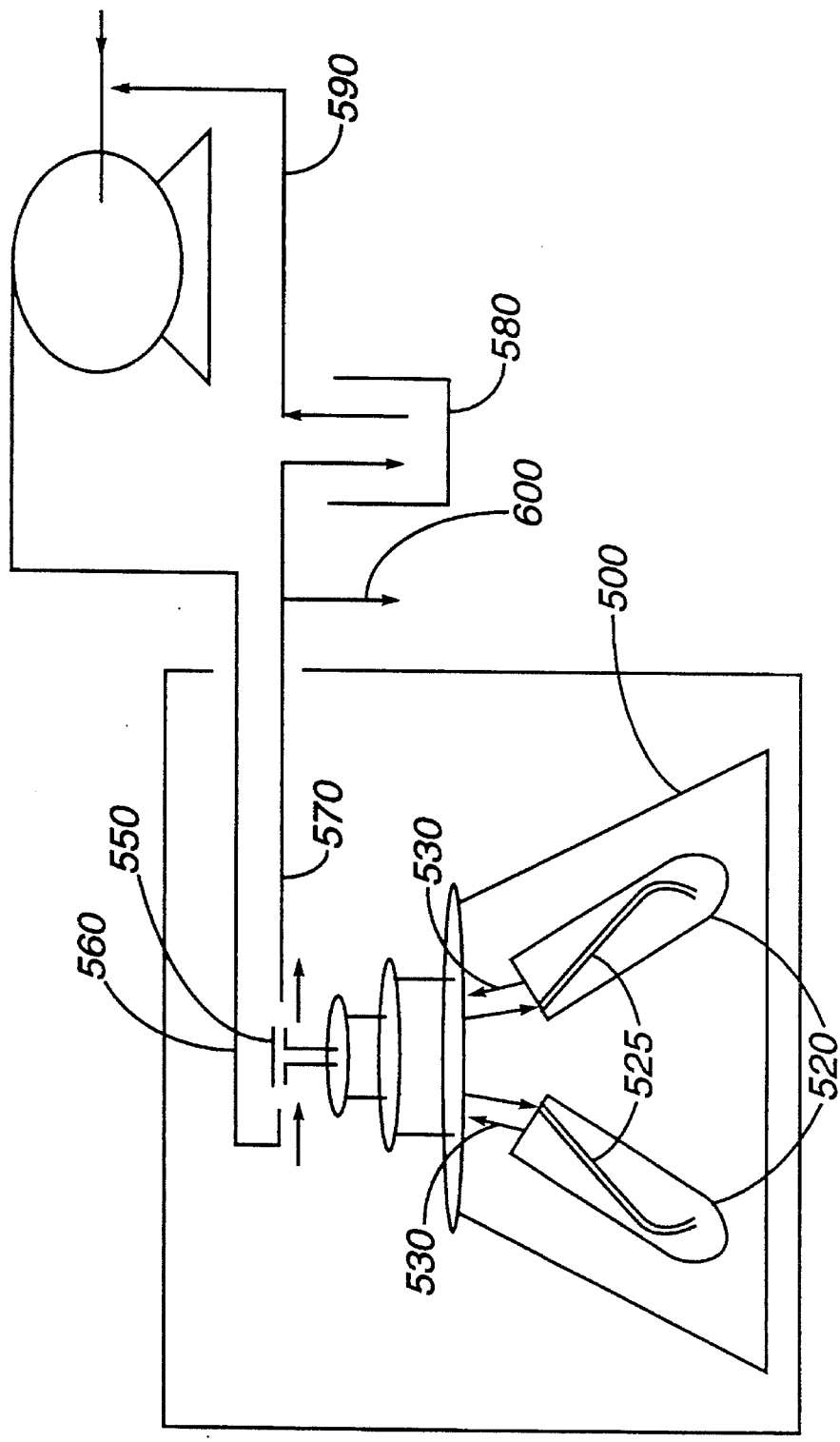
FIG. 13 is an illustration of an embodiment of a continuous centrifugal system.

A schematic of a working model of a continuous centrifugal reactor system designed to work for such a two-phase micelle system with the light phase organic and the heavy phase containing reversed micelles is shown in FIG. 13. Reactor 500 is a refrigerated centrifuge (Sorvall RC5B Superspeed) with a continuous rotor (KSB). Two centrifuge tubes 520 are employed in reactor 500, which have inlet tubes 525 and outlet tubes 530. A distribution assembly 550 connects to inlet and outlet feed lines (560 and 570, respectively). Inlet tubes 525 are preferably lengthened so that the feed enters centrifuge tubes 520 close to the bottom thereof (within the enzyme containing organic heavy phase). This design permits a greater contact time between the feed and the enzyme containing reversed micelles.

Feed (e.g., hexane solubilized pesticide) is pumped into the reactor at a controlled flow rate. The outlet is fed via outlet line 570 to a holding tank 580 where it is mixed and recycled to the reactor via recycle line 590. Product is drawn off via effluent line 600.

Figure 14:
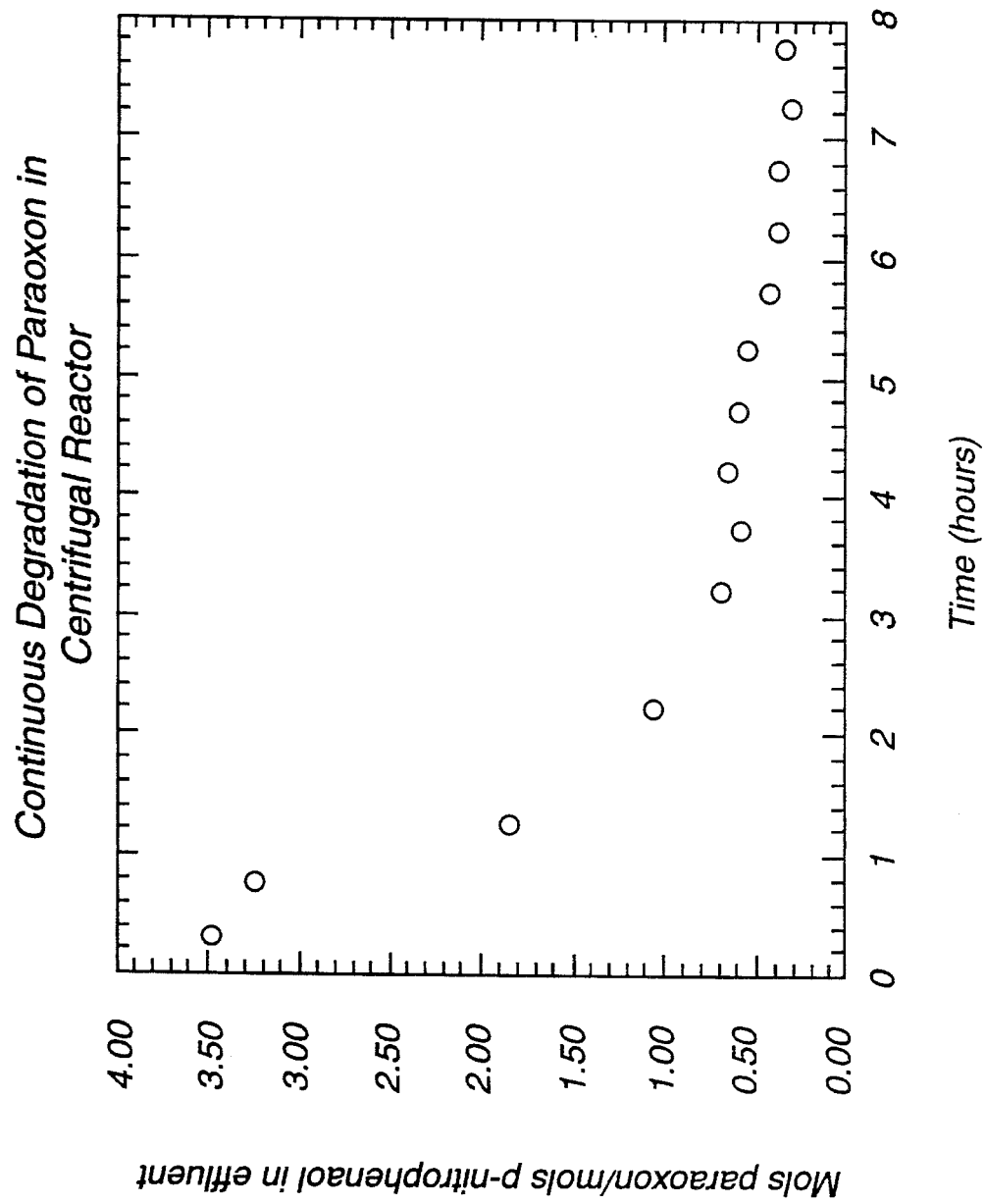
FIG. 14 is an illustration of pesticide conversion versus time in a continuous centrifugal bioreactor.

FIG. 14 shows the pesticide conversion to product as a function of time in the reactor operating with complete recycle. In this study, pesticide was fed to the reactor in a single pulse to study reactor performance. After less that three (3) hours, half of the pesticide was coverted to product. The product stream was shown to be completely free of enzyme and contained a low concentration (~10 mM) of Tween 85. The reaction rate is limited, however, by the extent of mixing between the phases. Reactor performance can be significantly enhanced by using means for increasing or extending the contact time between the phases as described above.

The two-phase system composed of reversed micelles in equilibrium with a predominantly organic phase has a number of useful properties for process design. Biocatalysts will partition significantly if not entirely into the reversed micelles, permitting large volumes of substrate-containing organic phase to be reacted without loss of catalyst. Minimization of biocatalyst loss is essential in the case of many biocatalysts because of prohibitive costs.

Also, substrates with low solubility in aqueous phase can be contained in high concentrations in this system. Higher concentrations lead to higher reaction rates and thus lower reactor volume. Thus the range of useful substrates for an enzyme can be broadened to include a number of reactions which previously would have been considered infeasible for bioconversion. Finally, continuous removal of product in an organic phase admits ease of product recovery because of the low boiling point of solvents. The solvent can also be easily recycled for reuse.

For many reactions the organic solvent/reversed micelle system may be more practical than the reversed micelle/aqueous system. If the biocatalyst partitions at all into the aqueous phase, some will be lost in the reactor effluent. In such cases, it may be necessary to employ an additional separation unit, such as ultrafiltration, to contain the biocatalyst. In any situation where the product partitions preferably into the organic phase, an organic solvent (e.g., hexane)/reversed micelle system would be the preferable choice.

Another example of a reaction well suited for the present centrifugal reactor system operating as an organic/reversed micelle system is the use of lipase to selectively react with one enantiomer of a racemic mixture thereby resulting in resolution of that enantiomer. Reversed micellar systems incorporating lipase can thus be used in the purification of racemic mixtures. Resolution of mixtures of R- and S-ibuprofen is a specific example for which lipase may be used.

The use of reversed micelles generally in a continuous centrifugal system provides a number of advantages over previous designs for commercial soil washing and other two-phase systems. Micelles are dynamic entities in that a continual process of collision, dimerization and reformation of the surfactant aggregates takes place. As a result of an ongoing exchange of micelle contents, on a time scale of seconds the dispersed aqueous phase is effectively continuous. The bulk aqueous phase in a two-phase micelle system, therefore, has a much greater contact with the organic phase via micelle interactions, as compared with a biphasic mixture without micelles. The rate of product removal in the aqueous phase or light organic phase (as appropriate) is significantly improved over a two phase system in the absence of complete mixing. This result enables the reactor to operate as a single stage operation, while previously, two stages were needed for mixing and settling.

From solubilization studies, reversed micelles have shown their ability to contain high concentrations of protein. The water pool composition can be designed to maximize the partitioning of protein from the aqueous bulk phase. Properties of the water such as ionic strength, pH and salt type can affect the protein content of the water pools. Indeed, in some systems even 100% of the protein remains in the micelle phase. As a result, the organic phase of a two-phase micelle system has the capacity to both dissolve contaminants and degrade them. In this way, what is transferred to the water pool has already been degraded, which prevents unreacted pollutants from passing out with the contacted feed. Another advantage of maintaining the enzyme in the organic phase is to prevent loss of expensive enzyme in the aqueous effluent.

Many reversed micellar systems are suitable for enzyme catalyzed reactions in the present reactor system. Examples of such systems are provided in Table 3 below.

TABLE 3

| Surfactant | Solvent (% v/v water) | Enzyme |
|---|---|---|
| AOT | isooctane (0.5–2.3) | α-chymotrypsin |
| | | lysozyme |
| | | LADH |
| | | lipoxygenase |
| | | lipases |
| | | cytochrome c |
| | n-octane (2.3) | α-chymotrypsin |
| | (2.3) | trypsin |
| | (1.0–5.0) | trypsin |
| | (1.0–1.6) | ribonuclease |
| | (0.5–1.8) | peroxidase |
| | (0.2–3.6) | lipases |
| | (various) | lipoxygenase |
| | | D-amino acid oxidase |
| | heptane (0.5–5) | α-chymotrypsin |
| | (5.0) | trypsin |
| | heptane mixed with | alkaline phosphatase |
| | phospholipids | lipase from |
| | (0.5–5.0) | chromobacterium |
| | | viscosum |
| CTAB | n-octane/chloroform | |
| | 1:1 (2.3) | α-chymotrypsin |
| | (2.3) | trypsin |
| | n-octane/chloroform | dehydrogenases |
| | 1:1 | |
| | octane, benzene | |
| | hexane, decane | dehydrogenases |
| | dodescane/n-hexanol | |
| | 9:1 (09–3.8) | |
| | hydrocarbons/ | α-chymotrypsin |
| | n-hexanol 9:1 | |
| | isooctane/chloroform 1:1 | lysozyme |
| | (1.8) | |

TABLE 3-continued

| Surfactant | Solvent (% v/v water) | Enzyme |
|---|---|---|
| | isooctane/butanol 1:4 (1.8) | |
| | heptane/chloroform 1:1 | α-chymotrypsin LADH lipase from chronobacterium visconsum |
| $C_{12}E_4$ | isooctane (0.1–0.5) | lysozyme |
| Brij-56[190] | heptane (0.5–2.0) | α-chymotrypsin |
| | hydrocarbons/n-hexanol 16 (0.5–3.0) | α-chymotrypsin |
| | cyclohexane (0.1–1.3) | pyrophosphatase |
| | cyclohexane (4) | lactate dehydrogenase |
| Brij-96 | cyclohexane | pyruvate kinase peroxidase |
| | octane | firefly luciferase |

The present centrifugal reactive system is not, however, limited to enzyme catalyzed reactions. Any catalyst that can be partitioned into one phase of a multiphase system is suitable. Aqueous soluble rhodium based catalysts, for example, can be utilized in reverse micellar systems for hydrogenation reactions such as the conversion of N-acetamidoacrylic acid to alanine.

The present centrifugal reactor system is also well suited for bioconversions in aqueous/aqueous two-phase systems. An example of a bioconversion in an aqueous/aqueous two phase system is the cellulase-catalyzed enzymatic degradation of cellulose can be described as an example. An aqueous feed of cellulose can be fed to a two phase system containing one phase of aqueous solution, and another of Dextran (5%)-PEG 20000 (3%) in which the enzyme is solubilized. The cellulose will preferentially partition into the dextran phase, whereupon the enzyme will degrade the cellulose to its monomeric component, glucose. The glucose, however, is preferentially soluble in the phase not containing dextran-PEG. Thus the product will pass into the phase not containing the enzyme, and can be removed in the continuous centrifuge reactor from the system. Continuous removal of product from the system will also enable a greater extent of conversion than in a batch reactor, particularly in the frequent case where the enzyme is inhibited by the product.

Moreover, any soluble catalyst system such as rhodium based catalysts complexes can be covalently attached to polymers such as PEG in aqueous/aqueous two-phase systems to effect a desired reaction in the PEG catalyst rich phase.

B. Continuous Centrifugal Multiphase Extraction.

In the operation of the present centrifugal system for extraction of a predetermined component, one phase of a two phase system preferably comprises an affinity means for preferentially partitioning a desired component or components into that phase. Preferably that component is substantially completely or completely partitioned into the phase of the affinity means. The aqueous nature of the water pools of reversed micellar systems, for example, enable preferential extraction of proteins. Such reverse micelles can be "tuned" to effect a desired extraction. Similarly, an aqueous mixture of one phase of an aqueous/aqueous two-phase system can act to preferentially partition a protein into that phase.

In general, any agent that is predominantly present in one phase of a multiphase system and acts to preferentially partition a component of interest into that phase can act as an affinity means. Receptors, for example, can be used as affinity means for the extraction of hormones. Antibodies can be used as affinity means for the extraction of antigents. Antibodies can also be used as affinity means for the extraction haptens (small organic molecules that bind to other molecules). Dyes can be used as affinity means for the extraction of protein. Lectin can be used as affinity means for the extraction of sugar. Concanavalin A can be used as an affinity means for the extraction of glycoproteins. Proteins can be used as affinity means for the extraction of inhibitors, activators and metals. Generally, the converse of the above examples is also feasible. Haptens, for example, can be used as an affinity means in a multiple-phase system for the extraction of antibody.

Although the water pools of micelles act themselves as affinity means, other affinity means such as those described above and others may be contained within such water pools to preferentially partition a constituent. Concanavalin A, for example, may be used in reversed micelles for the extraction of glycoproteins. Affinity means may also be bound to a particular polymer in an aqueous/aqueous two-phase system. A particular inhibitor may, for instance, be bound to PEG in an aqueous/aqueous two-phase system to bind a protein.

In an example of the operation of a centrifugal system for protein extraction, a mixture of proteins, such as a cell broth from fermentation, is fed to the top of the chamber. The mixture contacts the light phase and the feed begins to separate by density according to the centrifugal force. Proteins partition to the light phase or the heavy phase depending on the properties of those phases and the proteins. Preferably, one of the phases comprises an affinity means such as described above. In continuous operation, both the heavy and light phases are passed out of the system where they can be recycled to achieve a high degree of separation. To optimize extraction, contact between the phases is preferably maximized before separation takes place as described above for the reactive system.

The centrifugal extraction of interleukin from a cell extract is an example of improved extraction of proteins into a second phase by utilizing affinity ligands in the phase in which the protein of interest will concentrate. A cell extract can be fed to an aqueous system consisting of two phases. One phase will be aqueous, the other phase preferably has a high concentration of PEG-iminodiacetic acid (PEG bound iminodiacetic acid), a chemical variant of PEG which can bind metal ions such as copper.

Thus, a two phase system can be designed in the centrifugal extractor in which one phase will have a high concentration of metal ion. These metal ions at a given pH and ionic strength, will have the ability to bind to a specific protein, the process of which forms the basis of the new technology of immobilized-metal affinity chromatography (IMAC). Under simply determined appropriate conditions a cell extract containing interleukin, an important protein with potential cancer-treatment utility, can be fed to the reactor. The interleukin will begin to concentrate in the PEG-immodiacitic acid rich phase where it is bound by the metal ion. Other proteins can be removed from the reactor by removal of the aqueous phase. This process, in which the pH temperature and ionic strength of the aqueous phase can be adjusted during a run, is thus the equivalent of IMAC. The specific advantage of the present method versus standard IMAC, is cost (PEG-IDA is inexpensive relative to immobilized metal support materials) and ease of scale-up.

In the case of extraction using a high affinity ligand to concentrate the desired compound or protein in the first phase, the binding event must be reversible to effect a continuous operation. By flowing the phase containing product-bound ligand followed by removal of the product in a regeneration step, the free ligand can be continuously fed to the reactor for reuse. The regeneration step is designed specifically for a particular ligand. For example, changing pH or ionic strength is a standard way of reducing the binding constant of antibodies and proteins, or the addition of a reducing agent such as EDTA can release a metal bound protein from an IMAC ligand. Once the product is released, it must be separated from the affinity means by ultrafiltration or another size exclusion means. Because the ligand is attached to a polymer chain, the separation is facilitated.

The present reaction/separation and extraction/separation systems offers the potential for lower cost as opposed to previous designs. The possibility of single stage operation reduces equipment cost over a mixer/settler combination. In addition, the complexity of previous systems such as hollow fiber systems requires higher initial expense as well as maintenance costs. In addition, hollow fibers would plug easily in the presence of solids, such as soil. Additional equipment for filtration and pulverization would be required. The proposed centrifugal reactor can easily be made of appropriate materials to assure long operating life and durability. The design is simple and easy to scale up.

Although the invention has been described in detail for the purposes of illustration, it is to be understood that such detail is solely for that purpose and that variations can be made therein by those skilled in the art without departing from the scope of the invention except as it may be limited by the claims.

What is claimed is:

1. A centrifugal reactor system, comprising:
   a. a chamber rotatable about an axis;
   b. a means for rotating said chamber about said axis;
   c. at least a first inlet means in communicative connection with said chamber for introducing a feed to said chamber, said feed containing at least one reactant; and
   d. at least a first outlet means in communicative connection with said chamber for removing liquid from said chamber;
   said chamber containing at least two liquid phases therein, said at least two liquid phases comprising a first phase and a second phase, said first phase and said second phase being in contact with each other within said chamber, said first phase comprising a catalyst system therein, said catalyst system selected to effect a desired reaction involving said at least one reactant of said feed, which reactant partitions into said first phase to contact said catalyst system and react to produce a reaction product, at least a portion of said reaction product partitioning into said second phase, said chamber being rotated at a tangential velocity to create sufficient centrifugal force to maintain a volume of said second phase as a substantially unmixed phase at a location of communicative connection of said first outlet means with said chamber, thereby enabling removal of an amount of said second phase from said chamber while minimizing loss of said catalyst system.

2. The centrifugal reactor system of claim 1 wherein said first phase comprises a surfactant and said catalyst system is contained in reversed micelles present within said first phase, said first phase being a continuous organic phase.

3. The centrifugal reactor system of claim 2 wherein said catalyst system comprises a biocatalyst.

4. The centrifugal reactor system of claim 3 wherein said biocatalyst comprises an enzyme.

5. The centrifugal reactor system of claim 4 wherein said enzyme is phosphotriesterase.

6. The centrifugal reactor system of claim 5 wherein said at least one reactant is selected from the group consisting of paraoxon, parathion and methyl paraoxon.

7. The centrifugal reactor system of claim 2 wherein said first phase comprises an organic phase, and said second phase comprises an aqueous phase.

8. The centrifugal reactor system of claim 7 wherein said first phase comprises hexane.

9. The centrifugal reactor system of claim 8 wherein said surfactant comprises polyoxyethylene sorbitan trioleate.

10. The centrifugal reactor system of claim 9 further comprising a cosurfactant in said first phase.

11. The centrifugal reactor system of claim 10 wherein said cosurfactant is selected from the group consisting of isopropanol and ethylene glycol.

12. The centrifugal reactor system of claim 11 wherein said catalyst system comprises phosphotriesterase.

13. The centrifugal reactor system of claim 12 wherein said at least one reactant is selected from the group consisting of paraoxon, parathion and methyl paraoxon.

14. The centrifugal reactor system of claim 2 wherein said first phase comprises a surfactant rich organic phase, and said second phase comprises an organic phase containing substantially no enzyme.

15. The centrifugal reactor system of claim 14 wherein said first phase and said second phase each comprise hexane.

16. The centrifugal reactor system of claim 15 wherein said surfactant comprises polyoxyethylene sorbitan trioleate.

17. The centrifugal reactor system of claim 16 further comprising a cosurfactant in said first phase.

18. The centrifugal reactor system of claim 17 wherein said cosurfactant is selected from the group comprising isopropanol and ethylene glycol.

19. The centrifugal reactor system of claim 1 further comprising a means disposed within said chamber for extending contact time between said first phase and said second phase.

20. The centrifugal reactor system of claim 19 wherein said means for extending contact time between said first phase and said second phase comprises a sieve system.

21. The centrifugal reactor system of claim 19 wherein said means for extending contact time between said first phase and said second phase comprises a baffle system.

22. The centrifugal reactor system of claim 1 wherein said at least two liquid phases comprise an aqueous/aqueous two-phase system.

23. The centrifugal reactor system of claim 22 wherein said catalyst system comprises a biocatalyst.

24. The centrifugal reactor system of claim 23 wherein said biocatalyst comprises an enzyme.

25. The centrifugal reactor system of claim 22 further comprising a means disposed within said chamber for extending contact time between said first phase and said second phase.

26. The centrifugal reactor system of claim 25 wherein said means for extending contact time between said first phase and said second phase comprises a sieve system.

27. The centrifugal reactor system of claim 25 wherein said means for extending contact time between said first phase and said second phase comprises a baffle system.

28. The centrifugal reactor system of claim 27 wherein said first phase comprises a solution of a water soluble polymer.

29. The centrifugal reactor system of claim 28 wherein at least one phase of said aqueous/aqueous two-phase system comprises polyethylene glycol (PEG).

30. The centrifugal reactor system of claim 29 wherein said catalyst system comprises an enzyme partitioned in said first phase.

31. The centrifugal reactor system of claim 29 wherein said catalyst system is attached to PEG.

32. The centrifugal reactor system of claim 28 wherein said catalyst system is attached to said water soluble polymer.

33. The centrifugal reactor system of claim 1 wherein an amount of liquid is continuously removed from said second phase.

34. The centrifugal reactor system of claim 1 wherein reaction product partitions into said second phase and is thereby removed from said chamber.

35. The centrifugal reactor system of claim 1 further comprising a second inlet means and a second outlet means, whereby said first phase is removed from said chamber via said second outlet means and recirculated to said chamber via said second inlet means.

36. The centrifugal reactor system of claim 35 wherein said first inlet means is positioned in the vicinity of said second outlet means and said second inlet means is positioned in the vicinity of said first outlet means to increase contact time between said first phase and said second phase.

37. A method of performing a catalyzed reaction in a multiphase system comprising the steps of:
   a. introducing a feed containing at least one reactant into a chamber rotatable about an axis, said chamber containing at two liquid phases therein, said at least two liquid phases comprising a first phase and a second phase, said first phase and said second phase being in contact with each other within said chamber, said first phase comprising a catalyst system therein, said catalyst system selected to effect a desired reaction involving said at least one reactant of said feed, which reactant partitions into said first phase to contact said catalyst system and react to produce product, at least a portion of said product partitioning into said second phase;
   b. rotating said chamber at a tangential velocity to create sufficient centrifugal force to maintain a volume of said second phase as a substantially unmixed phase at a location of communicative connection of an outlet means with said chamber; and
   c. removing an amount of said second phase from said chamber via said outlet means.

38. The method of claim 37 wherein said first phase comprises a surfactant and said catalyst system is contained in reversed micelles present within said first phase, said first phase being a continuous organic phase.

39. The method of claim 38 wherein said catalyst system comprises a biocatalyst.

40. The method of claim 39 wherein said biocatalyst comprises an enzyme.

41. The method of claim 40 wherein said first phase comprises a surfactant rich organic phase, and said second phase comprises an organic phase containing substantially no enzyme.

42. The method of claim 38 wherein said first phase comprises an organic phase, and said second phase comprises an aqueous phase.

43. The method of claim 38 wherein said first phase comprises a surfactant rich organic phase, and said second phase comprises an organic phase.

44. The method of claim 37 further comprising the step of extending contact time between said first phase and said second phase.

45. The method of claim 44 wherein contact time between said first phase and said second phase is extended using a sieve system disposed within said chamber.

46. The method of claim 44 wherein contact time between said first phase and said second phase is extended using a baffle system disposed within said chamber.

47. The method of claim 37 wherein said at least two liquid phases comprise an aqueous/aqueous two-phase system.

48. The method of claim 47 wherein said catalyst system comprises a biocatalyst.

49. The method of claim 48 wherein said biocatalyst comprises an enzyme.

50. The method of claim 47 wherein said first phase comprises a solution of a water soluble polymer.

51. The method of claim 50 wherein at least one phase of said aqueous/aqueous twophase system comprises polyethylene glycol (PEG).

* * * * *